(12) United States Patent
Stengele

(10) Patent No.: US 11,001,602 B2
(45) Date of Patent: *May 11, 2021

(54) DIARYLSULFIDE BACKBONE CONTAINING PHOTOLABILE PROTECTING GROUPS

(71) Applicant: Roche Diagnostics Operations, Inc., Indianapolis, IN (US)

(72) Inventor: Klaus-Peter Stengele, Reiskirchen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 111 days.

This patent is subject to a terminal disclaimer.

(21) Appl. No.: 16/171,970

(22) Filed: Oct. 26, 2018

(65) Prior Publication Data

US 2019/0112328 A1 Apr. 18, 2019

Related U.S. Application Data

(60) Division of application No. 15/425,329, filed on Feb. 6, 2017, now Pat. No. 10,150,791, which is a (Continued)

(30) Foreign Application Priority Data

Apr. 7, 2011 (EP) ........................................ 1161556

(51) Int. Cl.
*C07H 19/20* (2006.01)
*C07C 323/19* (2006.01)
(Continued)

(52) U.S. Cl.
CPC ........... *C07H 19/20* (2013.01); *C07C 319/14* (2013.01); *C07C 323/19* (2013.01); (Continued)

(58) Field of Classification Search
CPC ...... C07H 19/20; C07C 319/14; C07C 323/19
See application file for complete search history.

(56) References Cited

U.S. PATENT DOCUMENTS 4,540,827 A 9/1985 Forster et al.
4,744,812 A 5/1988 Parg et al.
(Continued)

FOREIGN PATENT DOCUMENTS

EP 0077961 A2 5/1983
EP 0295233 A1 12/1988
(Continued)

OTHER PUBLICATIONS

Burrell, Carmin, Photolabile Protecting Groups {PLPG}: Synthetic and Biological Applications, 2008, pp. 1-73.
(Continued)

*Primary Examiner* — Jezia Riley
(74) *Attorney, Agent, or Firm* — Stinson LLP

(57) ABSTRACT

The present disclosure relates to photoactivable protecting groups containing a diarylsulfide chromophore, a method for the synthesis thereof and their use as photoactivable protecting groups using maskless photolithography based array synthesis.

a) 2-(2-Nitro-4-ethyl-5-thiophenyl-phenyl)propanol ("PhSNPPOH") 2,5-Diethyl-bromobenzene

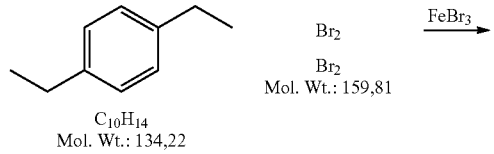

b) 2,5-Diethyl-4-nitro-bromobenzene

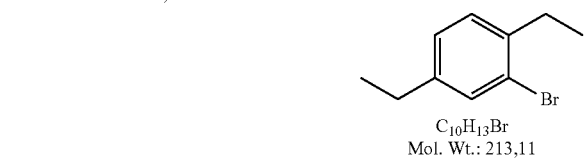

c) 2-(2-Nitro-4-ethyl-5-bromophenyl)propan-1-ol ("BrEtNPPOH")

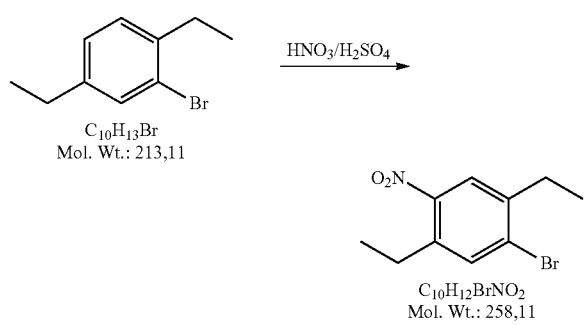

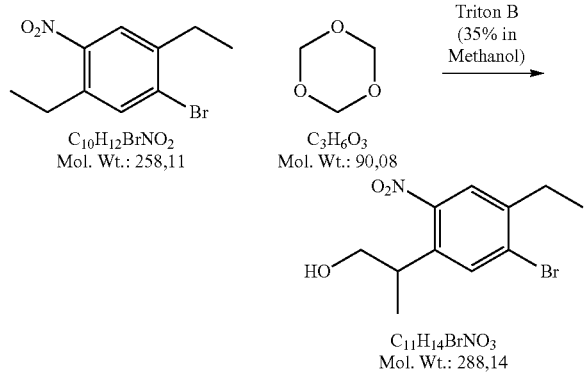

9 Claims, 20 Drawing Sheets

Related U.S. Application Data continuation of application No. 14/935,516, filed on Nov. 9, 2015, now abandoned, which is a continuation of application No. 14/061,297, filed on Oct. 23, 2013, now abandoned, which is a continuation of application No. 13/433,373, filed on Mar. 29, 2012, now abandoned.

(51) Int. Cl.

| | | |
|---|---|---|
| *C07C 323/32* | (2006.01) | |
| *C07H 19/02* | (2006.01) | |
| *C07D 231/12* | (2006.01) | |
| *C07D 235/28* | (2006.01) | |
| *C07D 207/16* | (2006.01) | |
| *C07D 213/70* | (2006.01) | |
| *C07C 319/14* | (2006.01) | |
| *C07H 1/00* | (2006.01) | |
| *C07H 19/06* | (2006.01) | |
| *C07H 19/10* | (2006.01) | |
| *C07H 19/16* | (2006.01) | |
| *C07K 1/04* | (2006.01) | |
| *C07K 7/08* | (2006.01) | |

(52) U.S. Cl.
CPC .......... *C07C 323/32* (2013.01); *C07D 207/16* (2013.01); *C07D 213/70* (2013.01); *C07D 231/12* (2013.01); *C07D 235/28* (2013.01); *C07H 1/00* (2013.01); *C07H 19/02* (2013.01); *C07H 19/06* (2013.01); *C07H 19/10* (2013.01); *C07H 19/16* (2013.01); *C07K 1/04* (2013.01); *C07K 7/08* (2013.01); *Y02P 20/55* (2015.11)

(56) References Cited

U.S. PATENT DOCUMENTS

| | | |
|---|---|---|
| 4,863,507 A | 9/1989 | Swithenbank et al. |
| 7,432,368 B2 | 10/2008 | Stengele |
| 2007/0232642 A1 | 10/2007 | Baxter et al. |
| 2008/0009630 A1 | 1/2008 | Gao et al. |
| 2008/0194624 A1 | 8/2008 | Baxter et al. |
| 2010/0048610 A1 | 2/2010 | Yamaguchi et al. |
| 2010/0292458 A1 | 11/2010 | Buehler et al. |

FOREIGN PATENT DOCUMENTS

| | | |
|---|---|---|
| EP | 1589024 A1 | 10/2005 |
| EP | 1810969 A1 | 7/2007 |
| WO | 1999015510 A1 | 4/1999 |
| WO | 2000021936 A1 | 4/2000 |
| WO | 2003065038 A3 | 8/2003 |
| WO | 2003066651 A1 | 8/2003 |
| WO | 2004074300 A3 | 9/2004 |
| WO | 2006024722 A3 | 3/2006 |
| WO | 2007092854 A3 | 8/2007 |

OTHER PUBLICATIONS

Corrie, John E. T., Photoremovable Protecting Groups Used for the Caging of Biomolecules, Dynamic Studies in Biology, 2005, pp. 1-94.

Givens, Richard S. et al., Photoremovable Protecting Groups, CRC Handbook of Organic Photochemistry and Dhotobiology, 2003, pp. 1-46, Chapter 69.

Fodor, Stephen P.A. et al., Light-Directed, Spatially Addressable Parallel Chemical Synthesis, Science, Feb. 15, 1991, pp. 767-773, vol. 251.

Hasan, Ahmad et al., "Photolabile Protecting Groups for Nucleosides: Synthesis and Photodeprotection Rates," Tetrahedron, 1997, pp. 4247-4264, vol. 53, No. 12.

Patchornik, A. et al., Photosensitive Protecting Groups, Journal of the American Chemical Society, Oct. 21, 1970, pp. 6333-6335, vol. 92, No. 21.

Pease, Ann Caviani et al., Light-generated oligonucleotide arrays for rapid DNA sequence analysis, Proceedings of he National Academy of Sciences, May 1994, pp. 5022-5026, vol. 91.

Taniguchi, N., Convenient Synthesis of Unsymmetrical Organochalcogenides Using Organoboronic Acids with Dichalcogenides via Cleavage of the S—S, Se—Se, or Te—Te Bond by a Copper Catalyst, Journal of Organic Chemistry, J007, pp. 1241-1245, vol. 72, No. 2.

Fig. 1

| Solvent | Half-life | Irradiation-wavelength | Experiment No. | Series | Exposure time |
|---|---|---|---|---|---|
| DMSO | 2.1 s | 390 nm | SB10-132 | 1324 | 2,4,6,8,12 s |
| DMSO | 2.4 s | 390 nm | SB10-132A | 1341 | 2,4,6 s |
| DMSO + 1 % Imidazol | 3.7 s | 390 nm | SB10-132 | 1325 | 2,4,6,8,12 s |
| NMP | 2.6 s | 390 nm | SB10-132 | 1326 | 2,4,6,8,12 s |
| NMP + 0.5 % Hydroxylamin | 1.8 s | 390 nm | SB10-132 | 1327 | 2,4,6,8,12 s |
| MeCN | 2.2 s | 390 nm | SB10-132 | 1328 | 2,4,6,8,12 s |
| MeCN + 1 % H$_2$O | 2.0 s | 390 nm | SB10-132 | 1329 | 2,4,6,8,12 s |
| MeCN + 1 % H$_2$O + 1 % Imidazol | 2.1 s | 390 nm | SB10-132 | 1330 | 2,4,6,8,12 s |
| MeCN + 16.3 % H$_2$O | 2.9 s | 390 nm | SB10-132A | 1335 | 2,4,6,8 s |
| MeCN + 16.3 % H$_2$O + 1 % Imidazol | 2.3 s | 390 nm | SB10-132A | 1336 | 2,4,6,8 s |
| Isopropanol | 4.1 s | 390 nm | SB10-132A | 1337 | 2,4,6,8 s |
| Isopropanol + 1 % Imidazol | 3.3 s | 390 nm | SB10-132A | 1338 | 2,4,6,8 s |
| Isopropanol + 12 % H$_2$O | 4.3 s | 390 nm | SB10-132A | 1339 | 2,4,6,8 s |
| Isopropanol + 12 % H$_2$O + 1 % Imidazol | 2.2 s | 390 nm | SB10-132A | 1340 | 2,4,6,8 s |

Fig. 2

| Solvent | Half-life | Irradiation-wavelength | Experiment No. | Series | Exposure time |
|---|---|---|---|---|---|
| DMSO | 3.3 min | 404 nm | SB10-128 | 1272 | 1,2,3,4 min |
| DMSO + 1 % Imidazol | 2.5 min | 404 nm | SB10-128 | 1273 | 1,2,3,4 min |
| DMSO | 3.8 min | 404 nm | SB10-130 | 1284 | 1,2,3,5 min |
| DMSO + 1 % Imidazol | 2.9 min | 404 nm | SB10-130 | 1285 | 1,2,3,5 min |
| NMP | 2.1 min | 404 nm | SB10-130 | 1286 | 1,2,3,5 min |
| NMP + 0.5 % Hydroxylamin | 1.8 min | 404 nm | SB10-130 | 1287 | 1,2,3,5 min |
| MeCN | 3.0 min | 404 nm | SB10-130 | 1288 | 1,2,3,5 min |
| MeCN + 1 % $H_2O$ | 3.1 min | 404 nm | SB10-130 | 1289 | 1,2,3,5 min |
| MeCN + 1 % $H_2O$ + 1 % Imidazol | 2.6 min | 404 nm | SB10-130 | 1290 | 1,2,3,5 min |
| Isopropanol | 5.6 min | 404 nm | SB10-139 | 1304 | 1,2,3,5 min |
| Isopropanol + 1 % Imidazol | 3.8 min | 404 nm | SB10-139 | 1305 | 1,2,3,5 min |

Fig. 3

| Compound | MW | M1 365 nm | M2 365 nm | M1 390 nm | M2 390 nm | M1 404 nm | M2 404 nm | ε(365 nm) | ε(390 nm) | ε(404 nm) |
|---|---|---|---|---|---|---|---|---|---|---|
| NPPOC-Phe | 449.49 | 0.066 | 0.069 | 0.014 | 0.016 | 0.003 | 0.004 | 302.4 | 67.0 | 16.3 |
| BTA-Phe | 553.53 | 0.095 | 0.094 | 0.019 | 0.019 | 0.005 | 0.005 | 522.4 | 104.4 | 26.7 |
| NaphS-Phe | 635.68 | 0.869 | 0.858 | 0.334 | 0.330 | 0.133 | 0.131 | 5489.3 | 2111.1 | 839.5 |
| PhS-Phe | 585.63 | 0.771 | 0.765 | 0.263 | 0.262 | 0.094 | 0.094 | 4497.8 | 1536.5 | 551.3 |
| PyS-Phe | 586.61 | 0.346 | 0.340 | 0.090 | 0.088 | 0.026 | 0.026 | 2014.0 | 522.6 | 151.8 |

Fig. 4
a) 2-(2-Nitro-4-ethyl-5-thiophenyl-phenyl)propanol ("PhSNPPOH")
2,5-Diethyl-bromobenzene
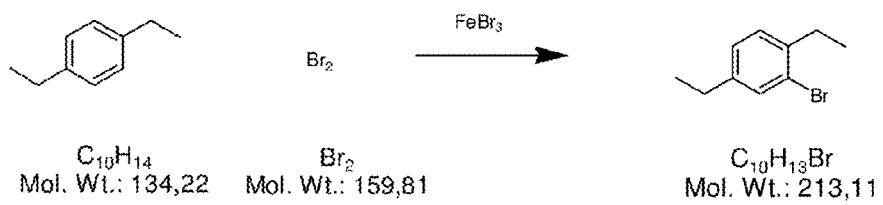
b) 2,5-Diethyl-4-nitro-bromobenzene
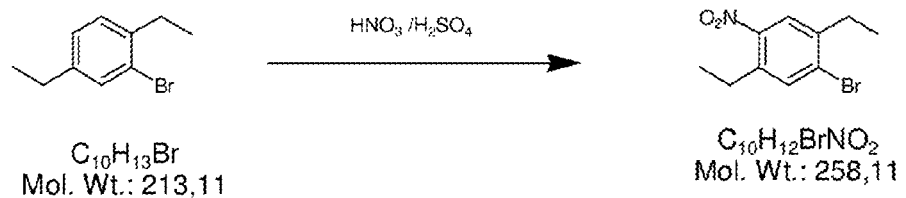
c) 2-(2-Nitro-4-ethyl-5-bromophenyl)propan-1-ol ("BrEtNPPOH")
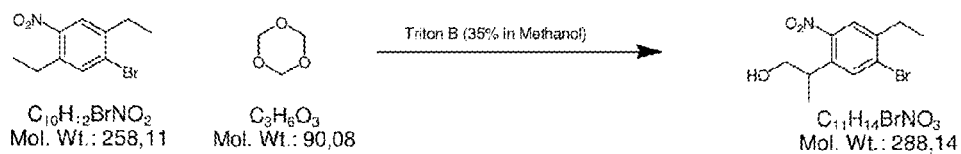

Fig. 4 cont.
d) 2-(2-Nitro-4-ethyl-5-thiophenylphenyl)propanol (PhSNPPOH)
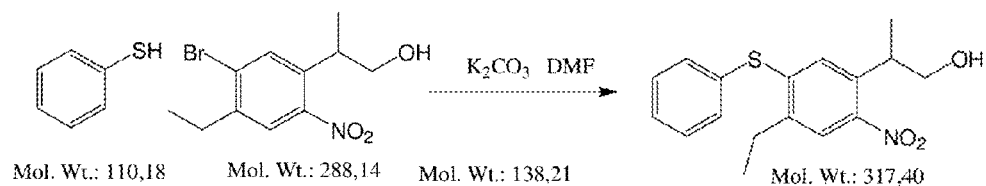
e) 2-(2-Nitro-4-ethyl-5-thiophenylphenyl)propanol Chlorocarbonate („PhSNPPOC-Cl")
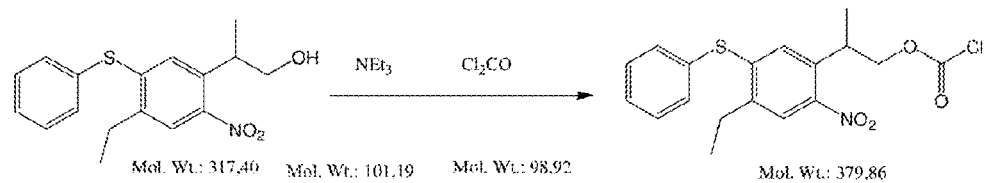
f) PhSNPPOC-Glycine-OH
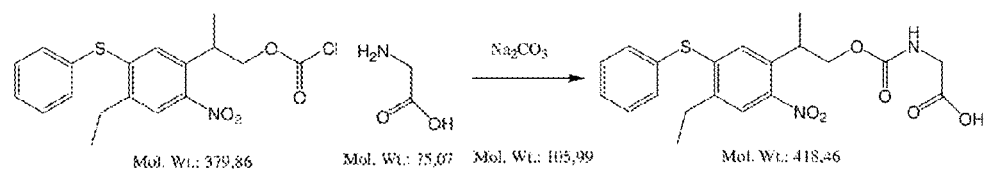

Fig. 4 cont.
g) PhSNPPOC-Proline-OH
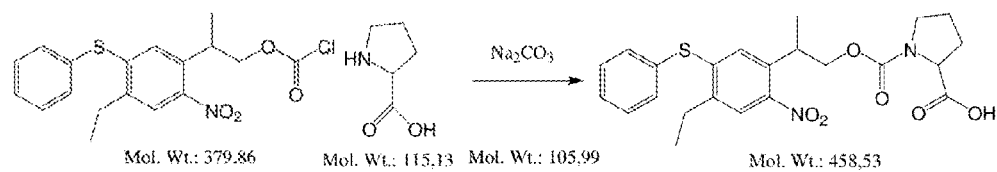
h) PhSNPPOC-Isoleucine-OH
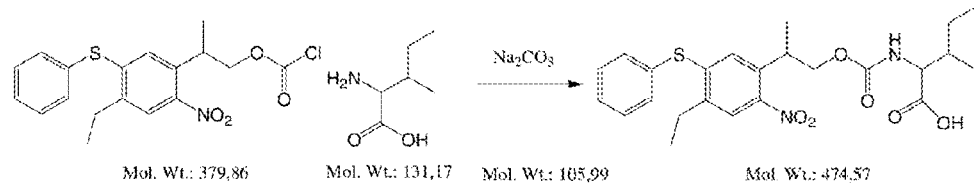
i) PhSNPPOC-AsparticAcid-OH
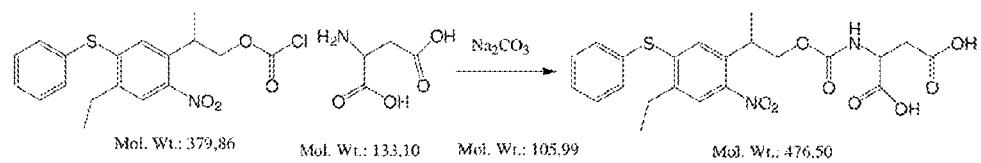

Fig. 4 cont.
j) PhSNPPOC-Asparagine-OH
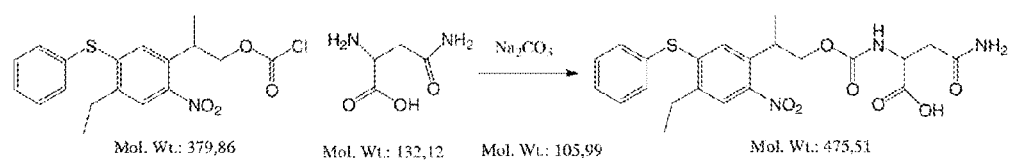
k) PhSNPPOC-Leucine-OH
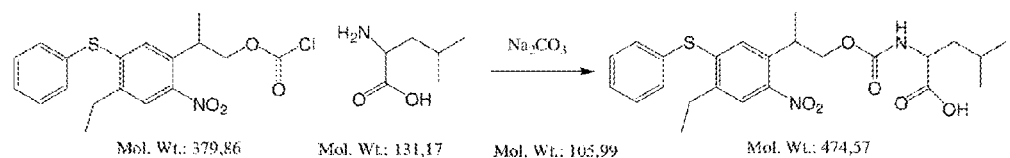
l) PhSNPPOC-$C_6$-Spacer
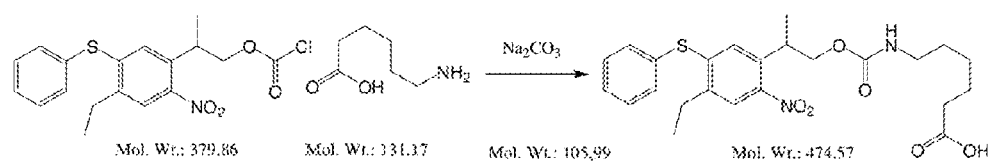

Fig. 4 cont.
m) PhSNPPOC-Lysine(Boc)-OH
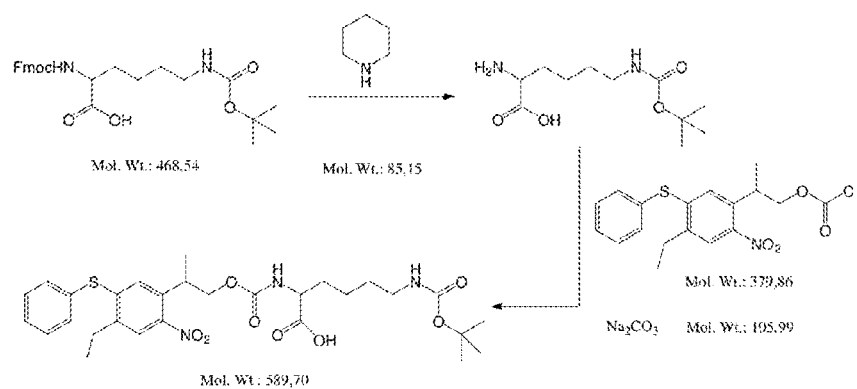
n) PhSNPPOC-Serine(t-Bu)-OH
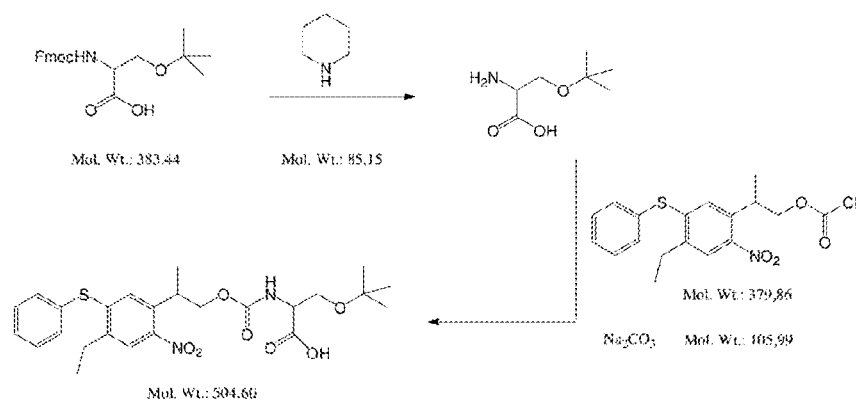

Fig. 4 cont.
o) PhSNPPOC-Threonine(t-Bu)-OH
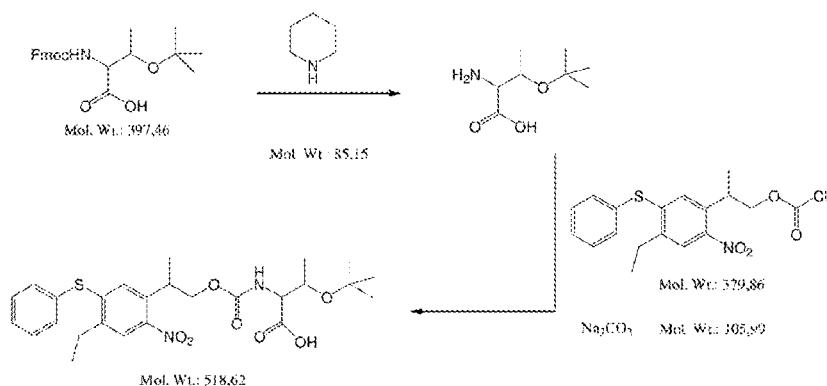
p) PhSNPPOC-Histidine(Trt)-OH
Step 1:
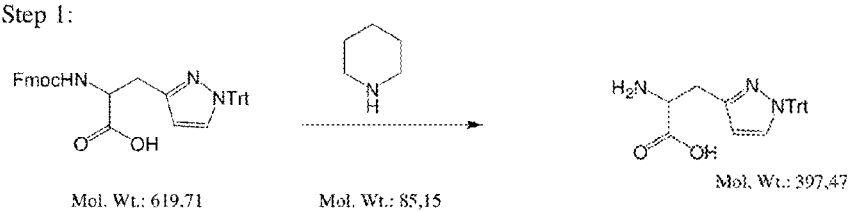
Step 2:
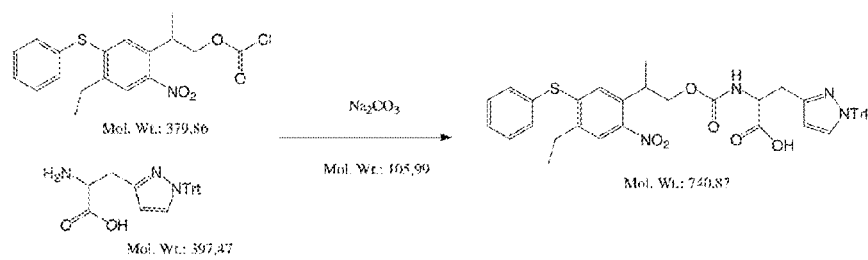

Fig. 5
a) 5′-PhSNPPOC-dT
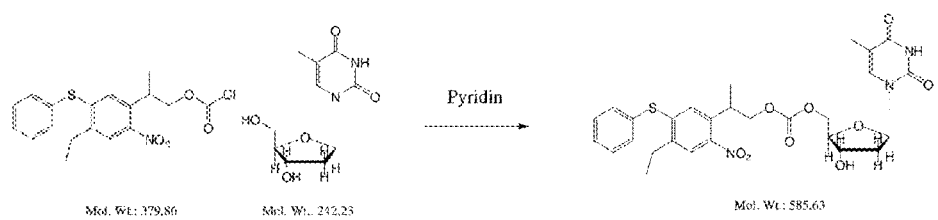
b) 5′-PhSNPPOC-dT-3′-PA
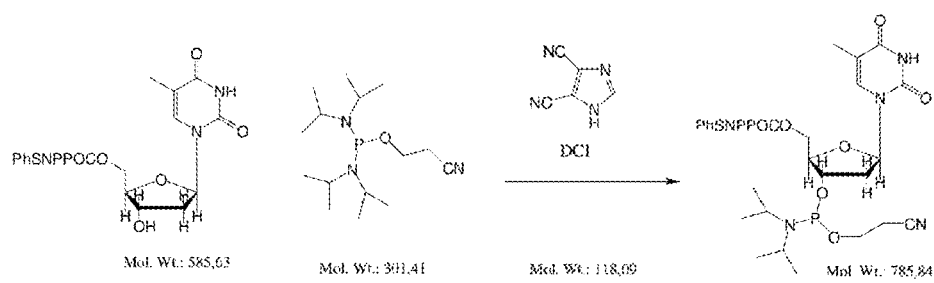
c) 5′-PhSNPPOC-dC^Ac
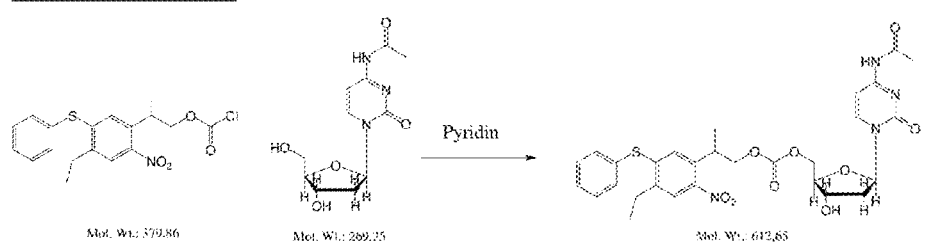

Fig. 5 cont.
d) 5'-PhSNPPOC-dC^Ac-3'-PA
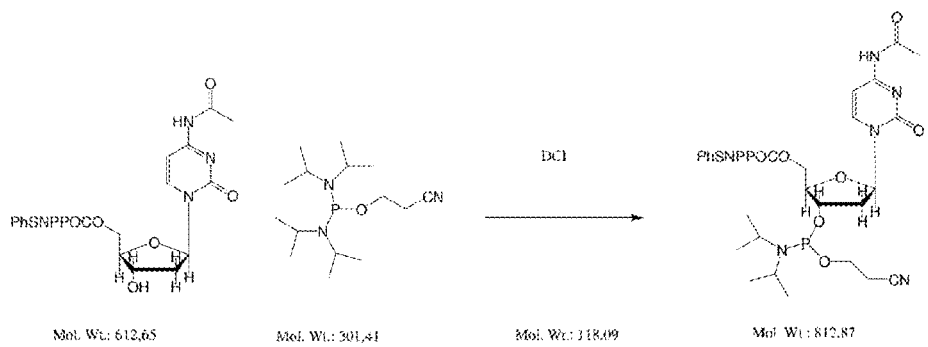
e) 5'-PhSNPPOC-dA^tac
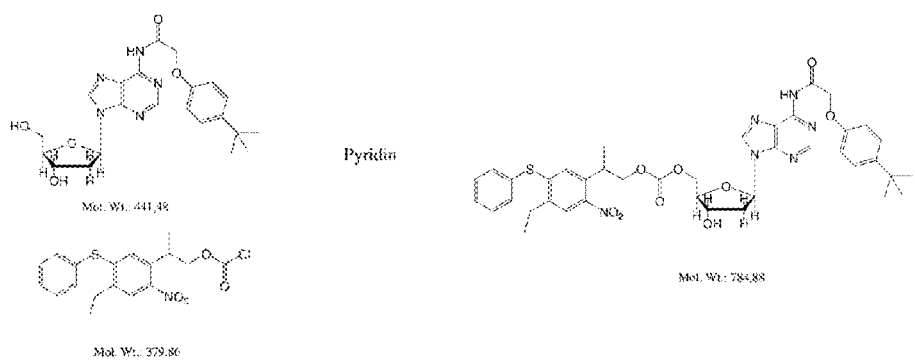
f) 5'-PhSNPPOC-dA^tac-3'-PA
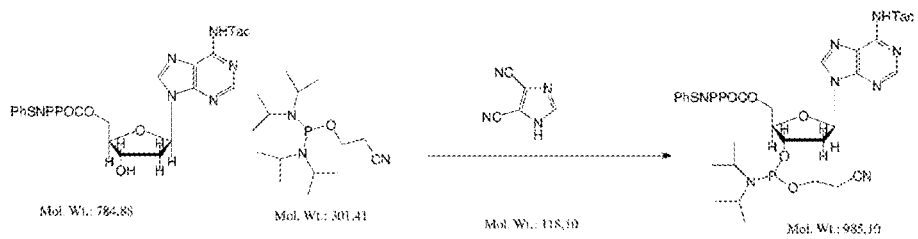

Fig. 5 cont.
g) 5´-PhSNPPOC-dG^(fac)
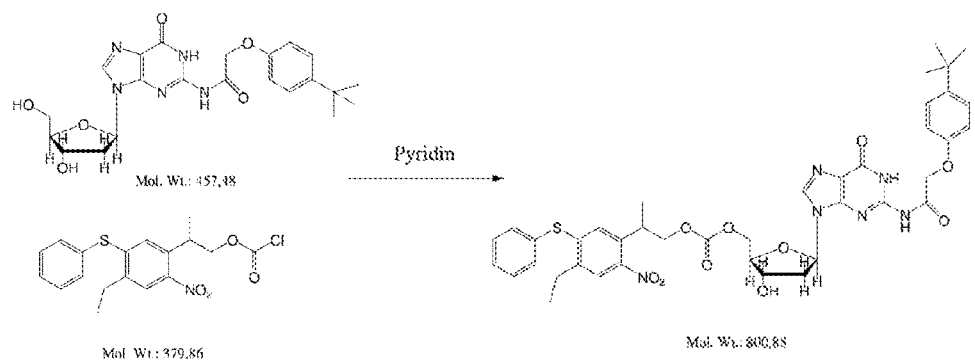
h) 5´-PhSNPPOC-dG^(fac)-3´-PA
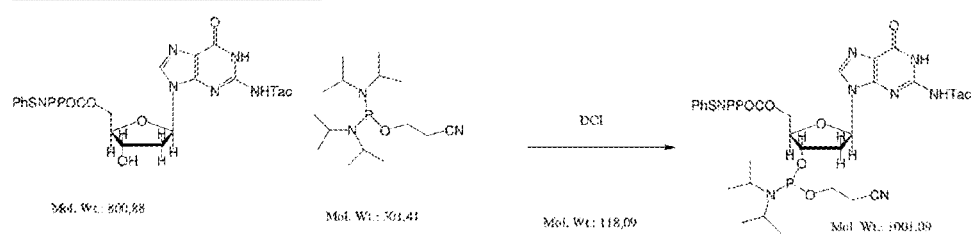

Fig. 6
a) 5-(t-Butylphenyl-thio)-4-ethyl-2-nitrophenyl-2´-propan-1´-ol (t-Butylthio-NPPOH)
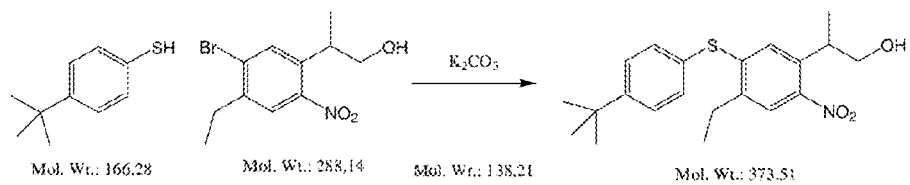
b) Naphthyl-thio-NPPOH
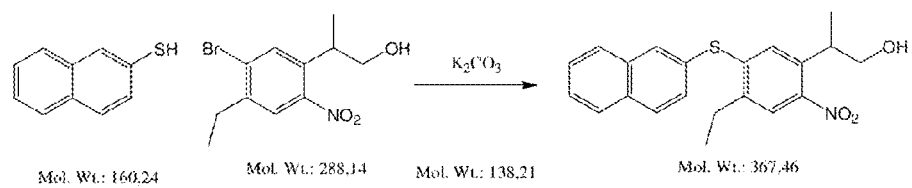
c) Nitrobenzimidazol-S-NPPOH
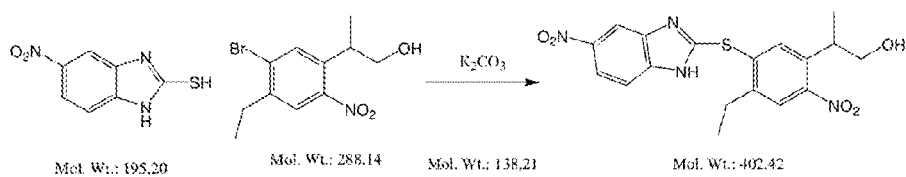
d) Pyridyl-S-NPPOH
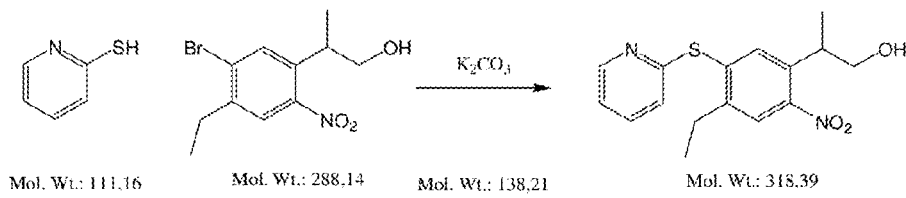

e) 2,5-Diethyl-4-phenoxy-nitrobenzene

Fig. 7
a) 3-Acetamido-ethylbenzol
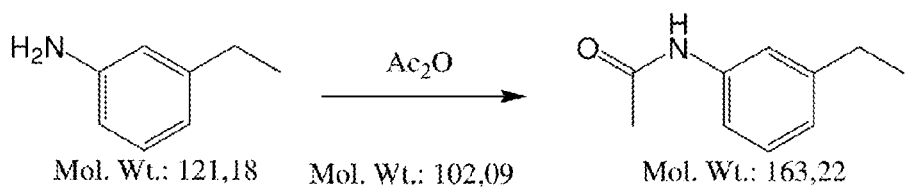
Mol. Wt.: 121,18    Mol. Wt.: 102,09    Mol. Wt.: 163,22
b) 3-Acetamido-6-nitro-ethylbenzol
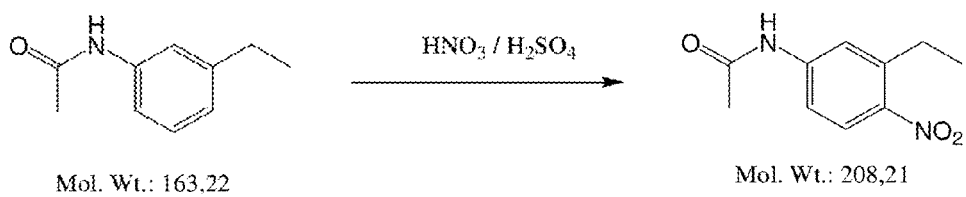
Mol. Wt.: 163,22    Mol. Wt.: 208,21
c) 3-Ethyl-4-nitro-aniliniumbromide
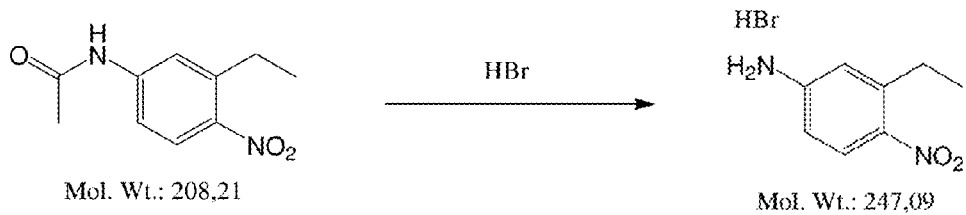
Mol. Wt.: 208,21    Mol. Wt.: 247,09

Fig. 7 cont.
d) 3-Brom-6-nitro-ethylbenzol
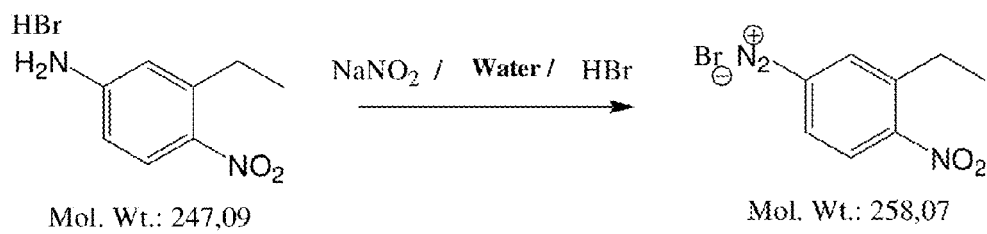
Sandmayer-Reaction
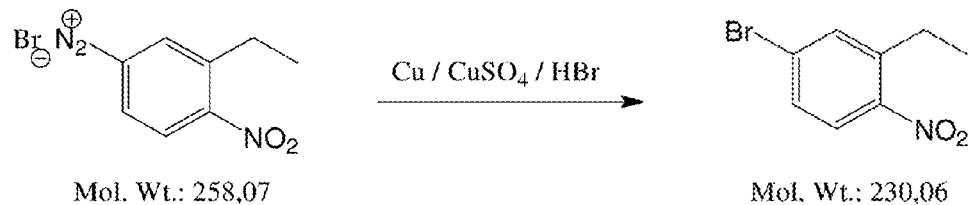
e) 2-(2-Nitro-5-brom-phenyl)propanol
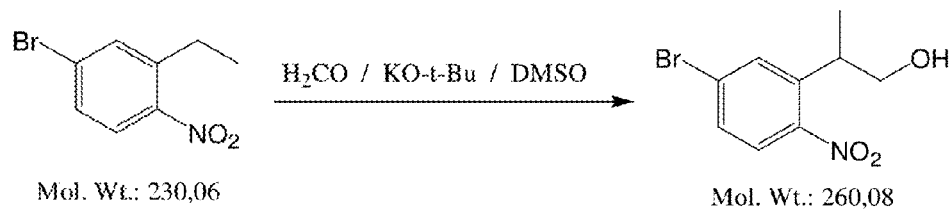

f) PhS-NPPOH

Mol. Wt.: 110.18   Mol. Wt.: 260.08   Mol. Wt.: 138.21                Mol. Wt.: 289.35 a)

b)

c)

DIARYLSULFIDE BACKBONE CONTAINING PHOTOLABILE PROTECTING GROUPS

PRIORITY CLAIM

This application is a divisional of U.S. patent application Ser. No. 15/425,329 filed Feb. 6, 2017, which is a continuation of U.S. patent application Ser. No. 14/935,516 (now abandoned) filed Nov. 9, 2015, which is a continuation of U.S. patent application Ser. No. 14/061,297 (abandoned) filed Oct. 23, 2013, which is a continuation of U.S. patent application Ser. No. 13/433,373 (abandoned) filed Mar. 29, 2012, which claims priority to European Patent Application No. 11161556.3, filed Apr. 7, 2011, the disclosures of which are hereby incorporated by reference in their entirety.

FIELD OF THE DISCLOSURE

The present disclosure relates to photoactivable protecting groups (PLPGs). More specifically, the present disclosure relates to the use of of PLPGs in biomolecule synthesis.

BACKGROUND OF THE DISCLOSURE

Photolabile protecting groups (PLPG) play an important role in blocking functional groups present in nucleosides, nucleotides, sugars and amino acids, which are used for the synthesis of biomolecules, e.g. nucleic acids and their derivatives, proteins, peptides and carbohydrates. Additionally, PLPG have the advantage that deprotection of the protected functional group can be performed simply via light exposure. Therefore, PLPG provide the basis for the photolithography based spatially resolved synthesis of oligonucleotides or peptides on solid supports. The major advantage of this technique is that high resolution microarrays can be produced. Such high resolution microarrays are of great significance for the analysis of biomolecules in medicine and pharmaceutical research, as they provide the possibility to perform high throughput and cost-effective analysis of multiple samples on a single array. Examples of PLPG used for oligonucleotide synthesis include, but are not limited to, α-methyl-6-nitropiperonyl-oxycarbonyl (MeNPOC), and 2-(2-nitrophenyl)-propoxycarbonyl (NPPOC). Examples of PLPG used for photolithography based peptide synthesis are for example nitroveratryloxycarbonyl (NVOC) and 2-nitrobenzyloxycarbonyl (NBOC).

Previous PLPG synthesis used light at a wavelength of approximately 365 nm or shorter for the deprotection of the protected functional groups. Light sources which are suitable to generate such wavelength, are e.g. mercury arc lamps, excimer lasers, UV-LEDs and frequency multiplied solid-state lasers. Such light sources are characterized by high purchase costs, provide limited luminous power and have a short life-time leading to high overall costs of operation. Since some of the above mentioned light sources contain hazardous substances, e.g. mercury, and appropriate actions to secure occupational safety and proper disposal are necessary, further increasing the costs.

Optical devices used for the photolithography based synthesis of oligonucleotides or peptides, such as micro mirror devices (WO 03/065038), are primarily designed for the visible wavelength range of approximately 380 to 780 nm. Such devices carry an antireflective or protective antiscratch coating optimized for transparency for the respective visible wavelength range. Thus, the near UV wavelength of 365 nm used for the deprotection of the functional groups protected with PLPG require optical devices which are optimized for near UV wavelengths. Since most of the optical devices are optimized for the use with visible light, such optimization often comprises removing the coating intended for the use with visible light from the optical devices and/or coating the optical device with materials intended for use with near UV or UV light.

Furthermore, many light sources produce a broad spectrum of wavelengths from the UV- to the IR-range, both of which have disadvantageous effects concerning the synthesis of biomolecules. As a result DNA or peptide microarrays might be of low quality due to undefined lengths of the synthesized DNA strands and peptides, respectively.

SUMMARY OF THE DISCLOSURE

PLPG are presented herein which are suitable for the deprotection of the functional groups using visible light. Consequently, harmless and cost-effective light sources as well as regular optical elements can be used for the photolithography based oligonucleotide and peptide synthesis.

The compounds of the present disclosure may be used for a variety of different applications. In one aspect, the disclosure is directed to the use of the compounds as photoactivable protecting groups using maskless photolithography. In one embodiment the compounds are used for the maskless photolithography based DNA array synthesis as intermediate or permanent OH-protecting group in nucleoside derivatives at the 3'-OH end or the 5'-OH end. Further, the compounds are useful for maskless photolithography based peptide array synthesis as NH-protecting group in amino acids. In another embodiment the compounds are useful for the maskless photolithography based peptide array synthesis as COOH-protecting group in amino acids and/or for the maskless photolithography based synthesis of carbohydrates as OH-protecting group and/or for orthogonal protecting group strategy as SH-protecting group. In another embodiment the compounds are used for maskless photolithography having a wavelength of 374 to 405 nm, for example a wavelength of 390 nm.

In another aspect, the disclosure is directed to a method for the synthesis of a diarylsulfide backbone containing photolabile protecting group as described above comprising the steps of Provision of p-diethylbenzene as a starting material Bromination of the phenylring Nitration of the obtained compound in Nitric- and Sulfuric Acid in the position para-to the Bromine Purification and crystallization Hydroxymethylation of the compound at the benzylic position Conversion of the aromatic bromine group to the arylsulfide using thiophenol Purification Conversion of the alcohol to chlorocarbonate Reaction of the chlorocarbonate with a nucleoside and reaction of the nucleoside with a phosphitylating agent, or Reaction of the chlorocarbonate with an amino acid derivative.

BRIEF DESCRIPTION OF THE FIGURES

The features of this disclosure, and the manner of attaining them, will become more apparent and the disclosure itself will be better understood by reference to the following description of embodiments of the disclosure taken in conjunction with the accompanying drawing.

FIG. 1 demonstrates half-lives of examples of PLPG according to the disclosure in various solvents used at a wavelength of 390 nm. Light exposure was performed for various time periods.

FIG. 2 demonstrates half-lives of examples of PLPG according to the disclosure in various solvents used at a wavelength of 404 nm. Light exposure was performed for various time periods.

FIG. 3 demonstrates certain UV absorption characteristics of PLPG.

FIG. 4 exemplifies synthesis pathways of disulfide-PLPG-amino acids.

FIG. 5 exemplifies synthesis pathways of disulfide-PLPG-nucleotides.

Figure 6:
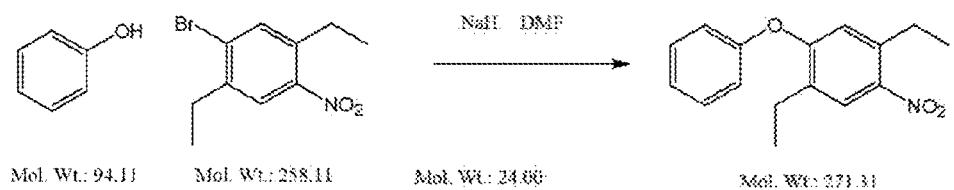
FIG. 6 exemplifies synthesis pathways of further PLPG according to the disclosure.
Figure 7:
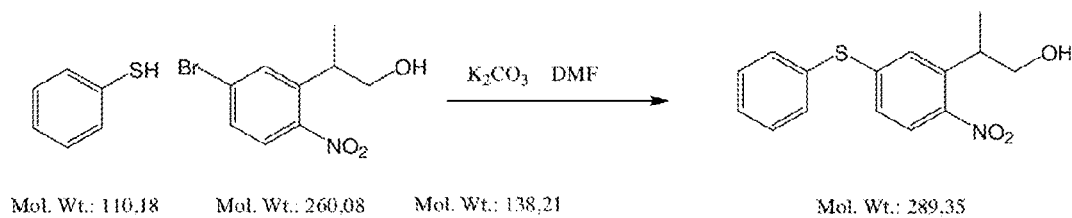
FIG. 7 exemplifies an alternative synthesis pathway of PLPG without further alkyl substituents.

Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

The following definitions are set forth to illustrate and define the meaning and scope of various terms used to describe the disclosure herein.

The term "unsubstituted" is used herein as known to the expert skilled in the art and refers to a hydrocarbon chain which fully consists of carbon and hydrogen.

The term "substituted" is used herein as known to the expert skilled in the art and refers to a replacement of a chemical group or substituent (typically H or OH) with a functional group, and particularly contemplated functional groups include electrophilic groups (e.g., C(O)—OR, C(X)—OH, etc.), nucleophilic (e.g., —NH2, —OH, —SH, —NC, etc.), ionic groups (e.g., —NH3-), polar groups (e.g., —OH), non-polar groups (e.g., aryl, alkyl, alkenyl, alkynyl, etc.), and halogens (e.g., —F, —Cl), and combinations thereof.

The term "protecting group" is used herein as known to the expert skilled in the art and refers to a substituent, functional group, ligand, or the like, which is bonded (e.g., via covalent bond, ionic bond, or complex) to a potentially reactive functional group and prevents the potentially reactive functional group from reacting under certain reaction conditions. Potentially reactive functional groups include, for example, amines, carboxylic acids, alcohols, double bonds, and the like. Protecting groups according to the disclosure are photo labile protecting groups, which include, but are not limited to, 2-Nitrobenzyloxycarbonyl (NBOC), 2-nitrophenyl-ethyloxycarbonyl (NPEOC), 2-(3,4-methylenedioxy-2-nitrophenyl)-propyloxy-carbonyl (MeNPPOC), 2-(3,4-methylenedioxy-2-nitrophenyl)-oxycarbonyl (MeNPOC), 2-(2-nitrophenyl)-propyloxycarbonyl (NPPOC), dimethoxy-benzo-inylyl-oxycarbonyl (DMBOC), 2-(2-nitrophenyl)-ethylsulfonyl (NPES), (2-nitrophenyl)-propylsulfonyl (NPPS), and the like.

The term "aryl" is used herein as known to the expert skilled in the art and refers to an aromatic residue consisting solely of hydrogen and carbon atoms, such as a phenyl (C6H5-), naphthyl (C10H7-) pyrenyl- or anthracenyl (C14H9-) residue. The aryl can be substituted or unsubstituted with e.g. alkyl groups, such as methyl, ethyl, n-propyl, iso-propyl, n-butyl, iso-butyl, or tert-butyl, or alkoxy—such as methoxy- ethoxy- or isopropoxy- or halogen atoms, such as bromide, chloride, or fluoride.

The term "heteroaryl" is used herein as known to the expert skilled in the art and refers to to a cyclic aromatic group having five or six ring atoms wherein at least one ring atom is selected from the group consisting of oxygen, sulfur, and nitrogen, and the remaining ring atoms are carbon. The heteroaromatic ring may form a fused heteroaromatic system together with other aryl- or heteroaryl-rings such as benzothiophene, benzimidazole, pteridine or alloxazine.

The term "alkyl" is used herein as known to the expert skilled in the art and refers to a univalent residue consisting only of carbon and hydrogen atoms. The alkyls form homologous series with the general formula $C_nH_{2n+1}$. The alkyl can be a straight or branched alkyl, for example the alkyl can be a secondary alkyl which is branched with the central carbon atom linked to two carbon residues or a tertiary alkyl which is branched with the central carbon atom linked to three carbon residues.

The letter A in the group -A-O— represents a "fragmentation linker" comprising from 1 to 2 linearly, covalently connected atoms such as methylene- or ethylene-. The term "fragmentation linker" is used herein as known to the expert skilled in the art and relates to a moiety which is used as a moiety in photochemistry that effects the light-induced fission of the PLPG by transforming the primary photoprocess into a chemical cleavage reaction. Accordingly, in a first aspect the divalent group -A- refers to a linking group which connects the functional group R2 with the nitrophenyl-chromophore. In one embodiment the 1 to 2 atom chain of the linking group A can be fully comprised of hydrogen and carbon atoms in form of a substituted or unsubstituted, branched or linear, saturated or unsaturated hydrocarbon chain.

The hydrocarbon chain can also be branched having one or more alkyl groups, wherein the alkyl group can be methyl, ethyl, n-propyl, iso-propyl, n-butyl, iso-butyl, or tert-butyl.

Such a hydrocarbon chain can also be substituted by e.g. halogen atoms. Accordingly, from 1 hydrogen atom to 3 hydrogen atoms of the respective hydrocarbon chain can be substituted through e.g. halogen.

The term "branched" in context with the definition of the term linking group is used herein as known to the expert skilled in the art and refers to the presence of a side-chain at the main chain of the molecule or moiety. Accordingly, a branched linking group can be a hydrocarbon chain as defined above having one or more alkyl groups as side chain, wherein the alkyl group is methyl, ethyl, n-propyl, iso-propyl, n-butyl, iso-butyl, or tert-butyl; in some embodiments the alkyl group is a methyl or ethyl group. In the branched hydrocarbon chain represented by A from one to all carbon atoms can have one or more alkyl groups as defined above.

The term "saturated" in context with the definition of the term linking group is used herein as known to the expert skilled in the art and relates to a linking group in which all members of the group are connected to the respective adjacent atom(s) through single bonds. Accordingly, a saturated hydrocarbon chain is represented by the formula —(CH2)n- with n being an integer ranging from 1 to 2.

The term "functional group" is used herein as known to the expert skilled in the art and refers to any of numerous combinations of atoms that form parts of chemical molecules, that undergo characteristic reactions themselves, and that in many cases influence the reactivity of the remainder of the molecule. Typical functional groups are hydroxyl, carboxyl, aldehyde, carbonyl, amino, azide, alkynyl, thiol and nitril.

The term "solid support" is used herein as known to the expert skilled in the art and refers to any insoluble and rigid or semi-rigid inorganic or organic material, often having a large surface area to which surface organic molecules can be attached through bond formation or absorbed through electronic or static interactions such as through bond formation through a functional group.

The term "biomolecule" is used herein as known to the expert skilled in the art and refers to any organic molecule that is produced by a living organism or to any artificially produced derivatives of such compounds, including large polymeric molecules such as proteins, polysaccharides, carbohydrates, lipids, nucleic acids and oligonucleotides as well as small molecules such as primary metabolites, secondary metabolites, and natural products.

The term "nucleic acid" is used herein as known to the expert skilled in the art and refers to a macromolecule composed of chains of monomeric nucleotides, wherein each nucleotide consists of three components: a nitrogenous heterocyclic base, which is either a purine or pyrimidine; a pentose sugar; and a phosphate group.

The term "natural amino acid" is used herein as known to the expert skilled in the art and refers to one of the 20 canonical amino acids used for protein biosynthesis as well as all amino acids which can be incorporated into proteins during translation (including pyrrolysine and selenocysteine). The 20 canonical amino acids include histidine, alanine, valine, glycine, leucine, isoleucine, aspartic acid, glutamic acid, serine, glutamine, asparagine, threonine, arginine, proline, phenylalanine, tyrosine, tryptophan, cysteine, methionine and lysine.

The term "non-natural amino acid" is used herein as known to the expert skilled in the art and refers to organic compounds that are not among those encoded by the standard genetic code or incorporated into proteins during translation. Furthermore, the term "non-natural amino acid" refers to organic compounds that do not occur naturally. Therefore, non-natural amino acids include amino acids or analogs of amino acids, but are not limited to, the D-isostereomers of amino acids, citrulline, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, γ-amino butyric acid, and derivatives thereof wherein the amine nitrogen has been mono- or di-alkylated.

The term "peptide" is used herein as known to the expert skilled in the art and refers to organic compounds made of amino acids arranged in a linear chain and joined together by peptide bonds between the carboxyl and amino groups of adjacent amino acid residues.

The term "amino group" is used herein as known to the expert skilled in the art and refers to primary (—NH2), secondary (—NHR1), or tertiary (—N R1 R2), and in cationic form, may be quaternary (—N R1 R2 R3). Examples of amino groups include, but are not limited to, —NH2, —NHCH3, —NHC(CH3)2, —N(CH3)2 and —N(CH2CH3) 2. Examples of cyclic amino groups include, but are not limited to, aziridino, azetidino, pyrrolidino, piperidino, piperazino, morpholino, and thiomorpholino.

The term "maskless photolithography" is used herein as known to the expert skilled in the art and refers to a technique for the synthesis of DNA- or peptide-microarrays without the use of photographic masks. The maskless photolithography uses an array of optical switching elements that are individually addressable and operable under software control. Examples of such optical switching elements are micro mirror devices. One example of a micro mirror device is the Digital Light Processor (DLP) from Texas Instruments, Inc.

In a first aspect, the disclosure is directed to photolabile protecting groups containing a diarylsulfide chromophore having the general formula:

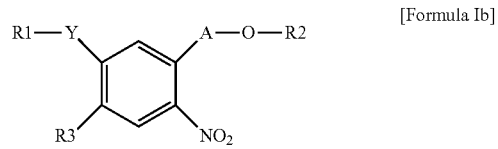

[Formula Ib]

wherein Y is S or O, and

A is selected from the group consisting of —CH$_2$—, —CH$_2$—CH$_2$—, —CH(CH$_3$)—, —CH(CH$_3$)—CH$_2$—, and R1 is an unsubstituted or substituted aryl- or heteroaryl-group, and R3 is H, a methyl group or an ethyl group, and wherein R2 is H, forms a phosphoramidite, H-phosphonate or phosphate triester, or wherein R2 is

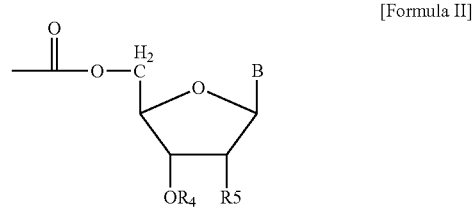

[Formula II]

or wherein R2 is

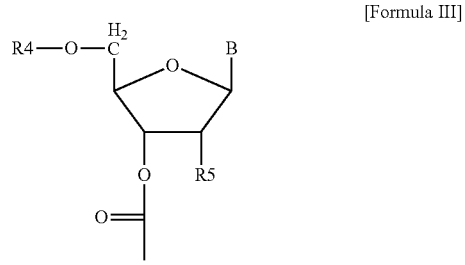

[Formula III]

wherein R4 is H, or OR4 forms a phosphoramidite, H-phosphonate or phosphate triester and wherein R5 is H, OH, a halogen or XR6, wherein X is O or S and R6 is H, an alkyl-group, aryl-group, or OR6 forms a phosphoramidite, phosphodiester, phosphotriester or H-phosphonate or an acetal or a silicone moiety, and wherein B is selected from the group consisting of adenine, cytosine, guanine, thymine, uracil, 2,6-diaminopurine-9-yl, hypoxanthin-9-yl, 5-methyl-cytosinyl-1-yl, 5-amino-4-imidazolecarboxylic acid-1-yl or 5-amino-4-imidazolecarboxylic acid amide-3-yl, wherein when B is adenine, cytosine or guanine the primary amino group optionally has a protecting group or when B is thymine or uracil at the $O^4$ position is optionally a protecting group, or wherein R2 is

[Formula IV]

wherein R7 is a natural amino acid, a non-natural amino acid or an amino acid derivative forming an urethan bond to formula Ib or wherein formula IV represents the carboxy function of a natural amino acid, a non-natural amino acid or an amino acid derivative, forming an ester bond to formula Ib.

In some embodiments, R1 is a phenyl-group, a tert-butyl-phenyl group, a 1- or 2-naphthyl-group, a 2-pyridyl-group an aminophenyl-group, an N-alkylaminophenyl-group, an N-Acylaminophenyl-group, a carboxyphenyl-group, a phenylcarboxylic ester or an amide, and/or A is —CH(CH3)-CH2- and/or R2 is a phosphoramidite or —P(OCH2CH2CN)(N-iPr2) and/or R4 is H and/or R5 is H and/or R7 is a natural amino acid. When B is selected from the group consisting of adenine, cytosine, guanine, thymine or uracil, or when B is adenine, cytosine or guanine the protecting group is typically selected from phenoxyacetyl-, 4-tert-butyl-phenoxyacetyl-, 4-isopropyl-phenoxyacetyl- or dimethylformamidino-residues, when B is adenine the protecting group is typically selected from benzoyl- or p-nitro-phenyl-ethoxy-carbonyl-(p-NPPOC)-residues, when B is guanine the protecting group is typically selected from isobutyroyl-, p-nitrophenylethyl (p-NPE) or p-NPEOC-residues and when B is cytosine the protecting group is typically selected from benzoyl-, isobutyryl- or p-NPEOC-residues.

In some embodiments, R1 is a phenyl-group, a tert-butyl-phenyl group, a 1- or 2-naphthyl-group, a 2-pyridyl-group, A is —CH(CH3)-CH2- and R3 is H or an ethyl group.

Certain embodiments of the present disclosure relate to diarylsulfide chromophore containing PLPG which can be used for the photolithography based oligonucleotide and peptide synthesis having the structure

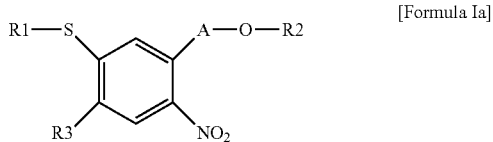

[Formula Ia]

wherein A is selected from the group consisting of —CH2-, —CH$_2$—CH$_2$—, —CH(CH$_3$)—, —CH(CH$_3$)—CH$_2$—, —CH2-CH(Alky,Aryl)- and —CH(CH3)-CH(Alkyl, Aryl)-

R1 is an unsubstituted or substituted aryl- or heteroaryl-group or a condensed aryl- or heteroaryl-group, and R3 is H, a methyl group or an ethyl group, and wherein R2 is

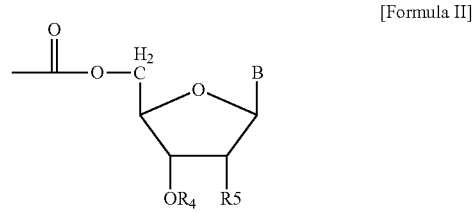

[Formula II]

or wherein R2 is

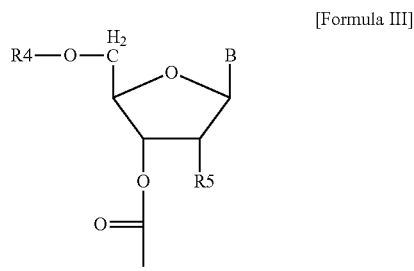

[Formula III]

wherein R4 is H, an alkyl-group, aryl-group, or OR4 forms a phosphoramidite, H-phosphonate or phosphate triester and wherein R5 is H, OH, a halogen or XR6, wherein X is O or S and R6 is an alkyl-group, aryl-group, or OR6 forms a phosphitamide-group, phosphodiester, phosphotriester or H-phosphonate or an acetal or a silicone moiety and wherein B is selected from the group consisting of adenine, cytosine, guanine, thymine, uracil, 2,6-diaminopurine-9-yl, hypoxanthin-9-yl, 5-methylcytosinyl-1-yl, 5-amino-4-imidazolecarboxylic acid-1-yl or 5-amino-4-imidazolecarboxylic acid amide-3-yl, wherein when B is adenine, cytosine or guanine the primary amino group optionally has a protecting group or when B is thymine or uracil at the $O^4$ position is optionally a protecting group, or wherein R2 is

[Formula IV]

wherein R7 is a natural amino acid, a non-natural amino acid or an amino acid derivative, including but not limited to α- or β-amino acids, forming an urethan bond to formula Ia, or wherein formula IV represents the carboxy function of a natural amino acid, a non-natural amino acid or an amino acid derivative, forming an ester bond to formula Ia, including but not limited to α- or β-amino acids.

In another embodiment compounds according to formula Ia are used, characterized in that R1 is a phenyl-group, a tert-butyl-phenyl group, a 1- or 2-naphthyl-group or a 2- or 4-pyridyl-group, A is —CH(CH3)-CH2-, R4 is H and R5 is H, R4 is H and R5 is OH or OSi(Alkyl3).

In another embodiment compounds according to formula Ia are used, characterized in that B is selected from the group consisting of adenine, cytosine, guanine, thymine, 5-methylcytosineor uracil.

In another embodiment compounds according to formula Ia are used, characterized in that, when B is adenine, cytosine or guanine the protecting group is phenoxyacetyl-, 4-tert-butyl-phenoxyacetyl-, 4-isopropyl-phenoxyacetyl- or dimethylformamidino-residues, when B is adenine the protecting group is a benzoyl-residue, when B is guanine the protecting group is a isobutyroyl-residue and when B is cytosine the protecting group is benzoyl- or isobutyroyl-residues.

In another embodiment compounds according to formula Ia are used, characterized in that R7 is a natural amino acid.

Some examples of the diarylsulfide chromophore containing PLPG which can be used for the photolithography based oligonucleotide and peptide synthesis have the structures:

[Formula V]

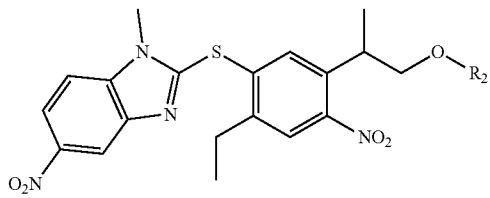

[Formula VI]

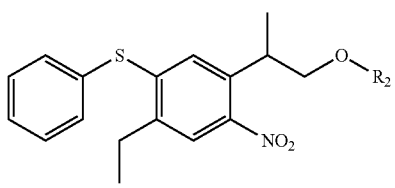

[Formula VII]

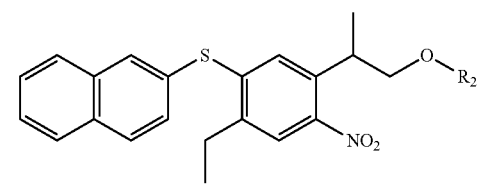

[Formula VIII]

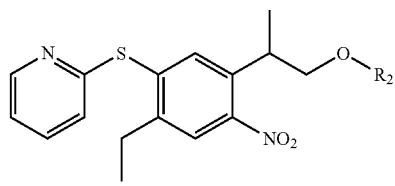

[Formula IX]

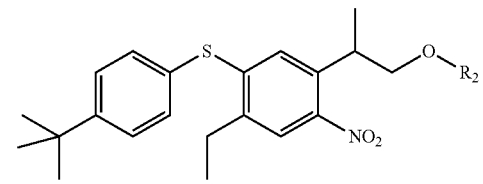

The present disclosure further relates to the use of the compounds according to formula Ia as photoactivable protecting group using maskless photolithography. In one embodiment of the disclosure micro mirror devices are used to perform a spatial selective exposure of the oligonucleotide and peptide microarrays to visible light in order to deprotect nucleotides and amino acids, respectively, in the exposed areas during the synthesis process. Deprotection of nucleotides and amino acids, respectively, lead to the release of the next linkage site for the respective next nucleotide or amino acid. The next nucleotide or amino acid which should be coupled to the released linkage site within the specific areas is simply added by its provision within a solvent plus an activating reagent which is poured onto the array. This strategy is repeated until oligonucleotides and oligopeptides, respectively, of the desired lengths and design are obtained. Using this strategy it is possible to produce highly dense microarrays of at least 10,000 features per cm2. This strategy may produce microarrays with even higher densities in the range of 100,000 to 500,000 features per cm2.

Various embodiments of the PLPG according to the disclosure can be removed by using visible light in a range from 375 nm to 420 nm, in the range from 390 to 405 nm, or in the range from 390 nm and 404 nm, respectively. These wavelengths can be generated using light sources which are much less expensive as compared to light sources necessary to perform deprotection in the near UV range at approximately 365 nm. In some embodiments, solid state lasers within the range from 375 nm to 420 nm, alternatively 390 nm and 404 nm, are used as light sources to remove the PLPG according to the disclosure. In other embodiments, LEDs (light emitting diodes) with sufficient emission within the range from 375 nm to 420 nm, or 390 nm and 404 nm, are used as light sources to remove the PLPG according to the disclosure. LEDs are one example of light sources that are low cost products as they are produced in high quantities, e.g. for the use in Blu-ray Players, that are useful in conjunction with the PLPG of the disclosure.

In further embodiments micro mirror devices are used which are optimized for the use of visible light in the range of 375 nm to 420 nm, or in the range of 390 to 410 nm, or in the range of 390 nm and 404 nm, respectively. In a further embodiment the coating of the micro mirror devices remain on the devices in order to be used with visible light. Devices that are used for UV- or near UV-light have to be optimized for that purpose, i.e. the coating on the micro mirror elements has to be removed by polishing.

In another embodiment, LCD displays or a beam splitter can be used as virtual masks between the light source and the synthesis area.

Photolithographic synthesis of the oligonucleotides and peptides, respectively, can be performed on a support, such as a solid support. The support can be made of any material known by the skilled person used for such a purpose, such as plastic, silicon, diamond carbon or glass. Examples of the material are optical grade polyolefin or optical grade microscope glass slides. The support can be provided in any form, such as beads, gels, plates, membranes, slides or chips. The support can be transparent or non-transparent, in various embodiments the support exhibits at least 30%, at least 60%, at least 90% light transmission at a wavelengths of between 375 nm to 410 nm.

The PLPG according to the disclosure can be used in any process for oligonucleotide synthesis known by the skilled person where protected nucleosides or nucleotides are necessary. The PLPG-nucleotides as described herein can be used for the synthesis of oligonucleotides in solution, further the PLPG-nucleotides as described herein can be used for the synthesis of oligonucleotides on a solid support. The synthesis can be performed by any standard method known in the state of the art. In some examples the synthesis can be performed by using photolithographic techniques, such as maskless techniques wherein a micro mirror device is used to expose light to spatial selected features on a microarray as explained above.

Solvents known by the skilled person can be used during oligonucleotide synthesis, such as acetonitrile.

Embodiments of the PLPG associated with nucleosides or nucleotides for oligonucleotide synthesis can be used in a concentration within the solvents of 1 mmol/L to 100 mmol/L, in a concentration of 10 mmol/L to 40 mmol/L, or in a concentration of 25 mmol/L.

The PLPG used with nucleosides or nucleotides can be used in connection with sensitizing agents known by the skilled person, which increase the effectiveness of the deprotection reaction. Examples of compounds useful as sensitizing agents are benzophenone, xanthone and thioxanthone derivates, like e.g. thioxanthen-9-one, alkylthioxanthen-9-ones, as for example isopropylthioxanthen-9-one, 2-ethylthioxanthen-9-one, 2-chloro-thioxanthen-9-one, 1,4-dimethoxythioxanthen-9-one.

Oligonucleotide microarrays can be used for a variety of purposes, including but not limited to sequence capturing, comparative genomic hybridization (CGH), CHIP-chip analysis, DNA-methylation analysis, gene expression analysis and comparative genome sequencing.

In another embodiment compounds according to formula Ia are used in the maskless photolithography based DNA array synthesis as intermediate or permanent OH-protecting group in nucleoside derivatives at the 3'-OH end or the 5'-OH end as carbon ester, wherein the synthesis can be performed in 3'-5'-direction or in 5'-3'-direction.

If the PLPG is located at the 5'-end, the nucleotide carries a phosphoramidite group on its 3'-end, which can be reacted with a free —OH group on the solid support to form a stable elongated oligonucleotide. After all oligonucleotides are synthesized, all PLPG are removed and the oligonucleotide still bound to the solid support has a free 5'-OH.

If however the PLPG is located at the 3'-end, the nucleotide carries a phosphoramidite group on its 5'-end, which can be reacted with any free —OH group on the solid support to form a stable elongated oligonucleotide. After all oligonucleotides are synthesized, all PLPG are removed and the oligonucleotide still bound to the solid support has a free 3'-OH.

While both types of immobilization allow for hybridization based assays, only the oligonucleotides that exhibit a free 3'-OH may be used for enzymatic reactions for detection, labeling, capping or elongation by ligation or enzymatic polymerization.

The PLPG according to the disclosure can further be used in any process for peptide synthesis known by the skilled person where protected amino acids are necessary. The amino acids can be non-natural amino acids, amino acid derivatives and/or natural amino acids. The PLPG as described herein can be used for the synthesis of oligopeptides in solution, or the PLPG as described herein can be used for the synthesis of oligopeptides on a solid support. The synthesis can be performed by any standard method known in the state of the art. For example, the synthesis can be performed by using photolithographic techniques, such as techniques where a micro mirror device is used to expose visible light to spatial selected features on a microarray as explained above.

It has been shown that the deprotection reaction is dependent on the solvent used during the peptide synthesis process. Solvents known by the skilled person can be used during peptide synthesis Polar solvents like dimethylsulfoxide (DMSO), n-methylpyrrolidone (NMP), acetonitrile (MeCN) or isopropanol are examples of solvents that can be used. Said solvents can contain certain additives, such as imidazole, hydroxylamine and water. Imidazole can be added at various concentrations, for example 0.1% to 3% (v/v), 0.5% to 1.5% (v/v), or 1% (v/v). Hydroxylamine can be added at concentrations of 0.1% to 3% (v/v), 0.2% to 1% (v/v), or 1% (v/v). Water can be added at concentrations of 0.1% to 20% (v/v 1% to 17% (v/v), or 1% (v/v). Examples of useful solvents are DMSO, DMSO+1% imidazole, NMP+ 0.5% hydroxylamine, MeCN+1% H2O, MeCN+1% H2O+ 1% imidazole, isopropanol+1% imidazole, isopropanol+ 12% H2O+1% imidazole.

The PLPG associated to amino acids for peptide synthesis can be used in a various concentrations within the solvents, such concentrations such as 0.1 mmol/L to 0.5 mmol/L, 0.2 mmol/L to 0.4 mmol/L, or the PLPG can be used in a concentration of 0.3 mmol/L.

The PLPG associated to amino acids can be used in connection with sensitizing agents known by the skilled person, which increase the effectiveness of the deprotection reaction.

Oligopeptide microarrays can be used for a variety of purposes, including but not limited to screening of antibody libraries, quantitative or qualitative analysis of biological samples, biomarker discovery, enrichment of scarce proteins, depletion of high abundant proteins, analysis of protein-protein-interactions, analysis of DNA-protein-interactions or RNA-protein-interactions.

In another embodiment compounds according to formula Ia are used for the maskless photolithography based peptide array synthesis as NH-protecting group in amino acids as urethan. The PLPG is used as NH-blocked free acid, activated ester, acid halogenide, anhydride, intermolecular or intramolecular as N-carboxy-anhydride (NCA).

In another embodiment the compounds according to formula Ia are used for the maskless photolithography based peptide array synthesis as COOH-protecting group in amino acids as ester for inverse direction of synthesis.

The PLPG according to the disclosure can further be used in any process known by the skilled person where protected sugars are necessary. The sugars used can be compounds, such as aldohexoses and aldopentoses. The PLPG as described herein can be used for the synthesis of carbohydrates, glycoproteins and proteoglycans in solution. In some embodiments, the PLPG as described herein can be used for the synthesis of carbohydrates, glycoproteins and proteoglycans on a solid support. The synthesis can be performed by any standard method known in the state of the art. For example, the synthesis can be performed by using photolithographic techniques, such as techniques where a micro mirror device is used to expose visible light to spatial selected features on a microarray as explained above.

Carbohydrate microarrays can be used for a variety of purposes, including but not limited to analysis of saccharide-protein-interactions, high-throughput analysis of proteins and cells, and analysis of glycans and their molecular interactions.

In another embodiment the compounds according to formula Ia are used for the maskless photolithography based synthesis of carbohydrates, glycoproteins, proteoglycans, and the like, as OH-protecting group as ether.

In another embodiment the compounds according to formula Ia are used as SH-protecting group for orthogonal strategies as ether, ester or thiocarbonate.

In another embodiment the compounds according to formula Ia are used as photoactivable protecting groups for releasing an biologically active structure for the initiation of a polymerase reaction or a ATP-dependent biochemical conversion.

The present disclosure further relates to the use of the compound according to formula Ia, characterized in that light is used for the maskless photolithography having a wavelength of 375 to 405 nm. Some embodiments use a wavelength of 390 nm.

The present disclosure further relates to a method for producing the diarylsulfide backbone containing PLPG which can be used for the photolithography based oligonucleotide and peptide synthesis, wherein the method comprises the following steps:

a) Providing as a starting material p-Diethylbenzene.

b) Bromination of the phenyl ring in one position by the action of molecular bromine and purification by distillation.

c) Nitration of the obtained compound in Nitric- and Sulfuric Acid in the position para- to the Bromine and isolation and purification by column chromatography on silica gel and crystallization.

d) Hydroxymethylation of the compound by the action of para-Formaldehyde in DMSO and Triton B at the benzylic position.

e) Conversion of the aromatic bromine group to the aryl sulfide by action of the appropriate thiophenol, thionaphthol etc in DMF potassium carbonate and catalytic amounts of copper(II) salt and purification by column chromatography on silica gel.

f) Conversion of the previous alcohol to the chlorocarbonate by action of triphosgen in THF and triethylamine.

g) Reaction of the chlorocarbonate with the appropriate nucleoside and further reacting the nucleoside with a phosphitylating agent to the appropriate phospshoramidite, or reaction of the chlorocarbonate with the appropriate amino acid derivative.

The following examples are provided to aid the understanding of the present disclosure, the true scope of which is set forth in the appended claims. It is understood that modifications can be made in the procedures set forth without departing from the spirit of the disclosure.

Further embodiments are included by the following items:

1. A compound of the formula

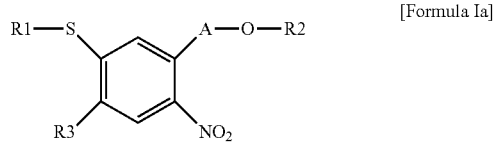

[Formula Ia]

wherein A is selected from the group consisting of $-CH_2-$, $-CH_2-CH_2-$, $-CH(CH_3)-$, $-CH(CH_3)-CH_2-$, and R1 is an unsubstituted or substituted aryl- or heteroaryl-group, and R3 is H, a methyl group or an ethyl group, and wherein R2 is

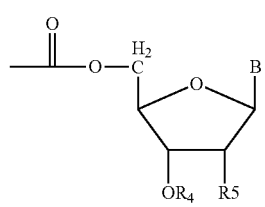

[Formula II]

or wherein R2 is

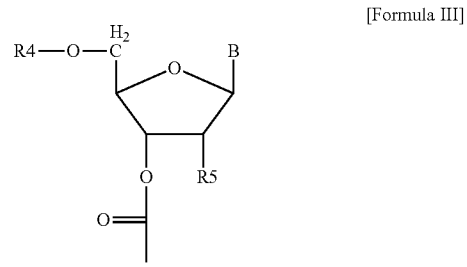

[Formula III]

wherein R4 is H, forms a phosphoramidite, H-phosphonate or phosphate triester, and
wherein R5 is H, OH, a halogen or XR6, wherein X is O or S and R6 is H, an alkyl-group, aryl-group, or OR6 forms a phosphoramidite, phosphodiester, phosphotriester, H-phosphonate or an acetal or silicone moiety, and
wherein B is selected from the group consisting of adenine, cytosine, guanine, thymine, uracil, 2,6-diaminopurine-9-yl, hypoxanthin-9-yl, 5-methylcytosinyl-1-yl, 5-amino-4-imidazolecarboxylic acid-1-yl or 5-amino-4-imidazolecarboxylic acid amide-3-yl, wherein when B is adenine, cytosine or guanine the primary amino group optionally has a protecting group or when B is thymine or uracil at the $O^4$ position is optionally a protecting group, or
wherein $R_2$ is

[Formula IV]

wherein R7 is a natural amino acid, a non-natural amino acid or an amino acid derivative forming an urethan bond to formula Ia, or
wherein formula IV represents the carboxy function of a natural amino acid, a non-natural amino acid or an amino acid derivative, forming an ester bond to formula Ia.

2. The compound according to item 1, characterized in that R1 is a phenyl-group, a tert-butyl-phenyl group, a 1- or 2-naphthyl-group or a 2-pyridyl-group.

3. The compound according to item 1 or 2, characterized in that A is —CH(CH3)-CH2-.

4. The compound according to items 1 to 3, characterized in that R3 is H or an ethyl group.

5. The compound according to items 1 to 4, characterized in that R4 is H and R5 is H.

6. The compound according to items 1 to 5, characterized in that B is selected from the group consisting of adenine, cytosine, guanine, thymine or uracil.

7. The compound according to items 1 to 6, characterized in that, when B is adenine, cytosine or guanine the protecting group is phenoxyacetyl-, 4-tert-butyl-phenoxyacetyl-, 4-isopropyl-phenoxyacetyl- or dimethylformamidino-residues, when B is adenine the protecting group is benzoyl- or p-nitro-phenyl-ethoxy-carbonyl- (p-NPPOC)-residues, when B is guanine the protecting group is isobutyroyl-, p-nitrophenylethyl (p-NPE) or p-NPEOC-residues and when B is cytosine the protecting group is benzoyl-, isobutyryl- or p-NPEOC-residues.

8. The compound according to items 1 to 4, characterized in that R7 is a natural amino acid.

9. Included in this disclosure is the use of the compound according to items 1 to 8 as photoactivable protecting group using maskless photolithography.

10. Included in this disclosure is the use of the compound according to item 7 for the maskless photolithography based DNA array synthesis as intermediate or permanent OH-protecting group in nucleoside derivatives at the 3'-OH end or the 5'-OH end.

11. Included in this disclosure is the use of the compound according to item 8 for the maskless photolithography based peptide array synthesis as NH-protecting group in amino acids.

12. Included in this disclosure is the use of the compound according to item 8 for the maskless photolithography based peptide array synthesis as COOH-protecting group in amino acids.

13. Included in this disclosure is the use of the compound according to item 8 for the maskless photolithography based synthesis of carbohydrates as OH-protecting group.

14. Included in this disclosure is the use of the compound according to item 8 for orthogonal protecting group strategy as SH-protecting group.

15. Included in this disclosure is the use of the compound according to items 8 to 13, characterized in that light is used for the maskless photolithography having a wavelength of 374 to 405 nm, for example 390 nm.

16. Also included in this disclosure is a method for preparing a diarylsulfide backbone containing photolabile protecting group according to one of the items 1 to 8 comprising the steps of
  a) Provision of p-diethylbenzene as a starting material
  b) Bromination of the phenyl ring
  c) Nitration of the obtained compound in Nitric- and Sulfuric Acid in the position para- to the Bromine
  d) Purification and crystallization
  e) Hydroxymethylation of the compound at the benzylic position
  f) Conversion of the aromatic bromine group to the arylsulfide using thiophenol
  g) Purification
  h) Conversion of the alcohol to chlorocarbonate
  i) Reaction of the chlorocarbonate with a nucleoside and reaction of the nucleoside with a phosphitylating agent, or
  Reaction of the chlorocarbonate with an amino acid derivative.

17. Also included is a method according to item 16, characterized in that R1 is a phenyl-group, a tert-butyl-phenyl group, a 1- or 2-naphthyl-group or a 2-pyridyl-group.

18. In other embodiments of the method according to item 16 or 17, characterized in that A is —CH(CH3)-CH2-.

19. In certain embodiments of the method according to item 16 to 18, R3 is H or an ethyl group.

The present disclosure further relates to diarylsulfide chromophore containing PLPG which can be used for the photolithography based oligonucleotide and peptide synthesis having the structure

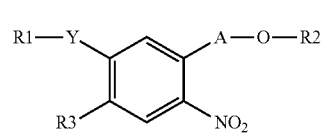

[Formula Ib]

wherein Y is S or O, and

A is selected from the group consisting of —CH2-, —CH$_2$—CH$_2$—, —CH(CH$_3$)—, —CH(CH$_3$)—CH$_2$—, —CH2-CH(Alky,Aryl)- and —CH(CH3)-CH(Alkyl, Aryl)-

R1 is an unsubstituted or substituted aryl- or heteroaryl-group or a condensed aryl- or heteroaryl-group, and R3 is H, a methyl group or an ethyl group, and wherein R2 is H, forms a phosphoramidite, H-phosphonate or phosphate triester, or wherein R2 is

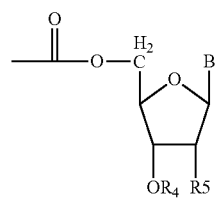

[Formula II]

or wherein R2 is

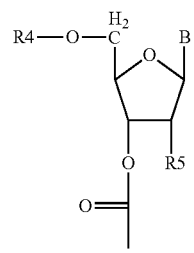

[Formula III]

wherein R4 is H, an alkyl-group, aryl-group, or OR4 forms a phosphoramidite, H-phosphonate or phosphate triester and wherein R5 is H, OH, a halogen or XR6, wherein X is O or S and R6 is an alkyl-group, aryl-group, or OR6 forms a phosphitamide-group, phosphodiester, phosphotriester or H-phosphonate or an acetal or a silicone moiety and wherein B is selected from the group consisting of adenine, cytosine, guanine, thymine, uracil, 2,6-diaminopurine-9-yl, hypoxanthin-9-yl, 5-methylcytosinyl-1-yl, 5-amino-4-imidazolecarboxylic acid-1-yl or 5-amino-4-imidazolecarboxylic acid amide-3-yl, wherein when B is adenine, cytosine or guanine the primary amino group optionally has a protecting group or when B is thymine or uracil at the O$^4$ position is optionally a protecting group, or wherein R2 is

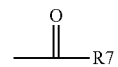

[Formula IV]

wherein R7 is a natural amino acid, a non-natural amino acid or an amino acid derivative, including but not limited to α- or β-amino acids, forming an urethan bond to formula Ib, or wherein formula IV represents the carboxy function of a natural amino acid, a non-natural amino acid or an amino acid derivative, forming an ester bond to formula Ib, including but not limited to α- or β-amino acids.

In another embodiment compounds according to formula Ib are used, characterized in that R1 is a phenyl-group, a tert-butyl-phenyl group, a 1- or 2-naphthyl-group, an aminophenyl-group, an N-alkylaminophenyl-group, an N-Acylaminophenyl-group, a carboxyphenyl-group, a phenylcarboxylic ester, an amide or a 2- or 4-pyridyl-group, A is —CH(CH3)—CH2-, R2 is a phosphoramidite or —P(OCH2CH2CN)(N-iPr2), R3 is H or an ethyl group, R4 is H and R5 is H, R4 is H and R5 is OH or OSi(Alkyl3).

In another embodiment compounds according to formula Ib are used, characterized in that B is selected from the group consisting of adenine, cytosine, guanine, thymine, 5-methylcytosine or uracil.

In another embodiment compounds according to formula Ib are used, characterized in that, when B is adenine, cytosine or guanine the protecting group is phenoxyacetyl-, 4-tert-butyl-phenoxyacetyl-, 4-isopropyl-phenoxyacetyl-or dimethylformamidino-residues, when B is adenine the protecting group is a benzoyl-residue, when B is guanine the protecting group is a isobutyroyl-residue and when B is cytosine the protecting group is benzoyl- or isobutyroyl-residues.

In another embodiment compounds according to formula Ib are used, characterized in that R7 is a natural amino acid.

The present disclosure further relates to the use of the compounds according to formula Ib as photoactivable protecting groups using maskless photolithography. In one embodiment of the disclosure micro mirror devices are used to perform a spatial selective exposure of the oligonucleotide and peptide microarrays to visible light in order to deprotect nucleotides and amino acids, respectively, in the exposed areas during the synthesis process. Deprotection of nucleotides and amino acids, respectively, lead to the release of the next linkage site for the respective next nucleotide or amino acid. The next nucleotide or amino acid which should be coupled to the released linkage site within the specific areas is simply added by its provision within a solvent plus an activating reagent which is poured onto the array. This strategy is repeated until oligonucleotides and oligopeptides, respectively, of the desired lengths and design are obtained. Using this strategy it is possible to produce highly dense microarrays of at least 10,000 and in certain embodiments 100,000 to 500,000 features per cm2.

Certain embodiments of the PLPG according to the disclosure can be removed by using visible light in a range from 375 nm to 420 nm, while certain embodiments can be removed in the range from 390 to 405 nm. Certain embodiments are removed via deprotection at wavelengths of 390 nm and 404 nm, respectively. Both wavelengths can be generated using light sources which are much less expensive as compared to light sources necessary to perform deprotection in the near UV range at approximately 365 nm. In some embodiments, solid state lasers within the range from 375 nm to 420 nm, or within the range of 390 nm and 404 nm, are used as light sources to remove the PLPG according to the disclosure. In some embodiments, LEDs (light emitting diodes) with sufficient emission within the range from 375 nm to 420 nm, or within the range of 390 nm and 404 nm, are used as light sources to remove the PLPG according to the disclosure. Especially LEDs are low cost products as they are produced in high quantities, e.g. for the use in Blu-ray Players.

In a further embodiment micro mirror devices are used, which are optimized for the use of visible light in the range of 375 nm to 420 nm, or in the range of 390 to 410 nm, or in the range of 390 nm to 404 nm, respectively. In a further embodiment the coating of the micro mirror devices remain on the devices in order to be used with visible light. Devices that are used for UV- or near UV-light have to be optimized for that purpose, i.e. the coating on the micro mirror elements has to be removed by polishing.

In another embodiment, LCD displays or a beam splitter can be used as virtual masks between the light source and the synthesis area.

Photolithographic synthesis of the oligonucleotides and peptides, respectively, can be performed on a support, for example a solid support. The support can be made of any material known by the skilled person used for such a purpose. Examples of materials useful for the support is are plastic, silicon, diamond carbon or glass. In some embodiments, plastic or glass is used as a support. In certain embodiments, as the material is optical grade polyolefin or optical grade microscope glass slides. The support can be provided in any form, such as beads, gels, plates, membranes, slides or chips. The support can be transparent or non-transparent. In some embodiments, the the support exhibits at least 30%, at least 60%, or at least 90% light transmission at a wavelengths of between 375 nm to 410 nm.

The PLPG according to the disclosure can be used in any process for oligonucleotide synthesis known by the skilled person where protected nucleosides or nucleotides are necessary. The PLPG-nucleotides as described herein can be used for the synthesis of oligonucleotides in solution, or the PLPG-nucleotides as described herein can be used for the synthesis of oligonucleotides on a solid support. The synthesis can be performed by any standard method known in the state of the art. For example, the synthesis can be performed by using photolithographic techniques, such as maskless techniques wherein a micro mirror device is used to expose light to spatial selected features on a microarray as explained above.

Solvents known by the skilled person can be used during oligonucleotide synthesis, such as acetonitrile.

The PLPG associated to nucleosides or nucleotides for oligonucleotide synthesis can be used at various concentrations within the solvents, such as in the range of 1 mmol/L to 100 mmol/L, 10 mmol/L to 40 mmol/L, or at a concentration of 25 mmol/L.

The PLPG associated with nucleosides or nucleotides can be used in connection with sensitizing agents known by the skilled person, which increase the effectiveness of the deprotection reaction. Examples of sensitizing agents useful for this disclosure are benzophenone, xanthone and thioxanthone derivates, like e.g. thioxanthen-9-one, alkylthioxanthen-9-ones, as for example isopropylthioxanthen-9-one, 2-ethylthioxanthen-9-one, 2-chloro-thioxanthen-9-one, 1,4-dimethoxythioxanthen-9-one.

Oligonucleotide microarrays can be used for a variety of purposes, including but not limited to sequence capturing, comparative genomic hybridization (CGH), CHIP-chip analysis, DNA-methylation analysis, gene expression analysis and comparative genome sequencing.

In another embodiment compounds according to formula Ib are used in the maskless photolithography based DNA array synthesis as intermediate or permanent OH-protecting group in nucleoside derivatives at the 3'-OH end or the 5'-OH end as carbon ester, wherein the synthesis can be performed in 3'-5'-direction or in 5'-3'-direction.

If the PLPG is located at the 5'-end, the nucleotide carries a phosphoramidite group on its 3'-end, which can be reacted with a free —OH group on the solid support to form a stable elongated oligonucleotide. After all oligonucleotides are synthesized, all PLPG are removed and the oligonucleotide still bound to the solid support has a free 5'-OH.

If however the PLPG is located at the 3'-end, the nucleotide carries a phosphoramidite group on its 5'-end, which can be reacted with any free —OH group on the solid support to form a stable elongated oligonucleotide. After all oligonucleotides are synthesized, all PLPG are removed and the oligonucleotide still bound to the solid support has a free 3'-OH.

The PLPG according to the disclosure can further be used in any process for peptide synthesis known by the skilled person where protected amino acids are necessary. The used amino acids can be non-natural amino acids, amino acid derivatives and/or natural amino acids PLPG as described herein can be used for the synthesis of oligopeptides in solution, or the PLPG as described herein can be used for the synthesis of oligopeptides on a solid support. The synthesis can be performed by any standard method known in the state of the art. For example, the synthesis can be performed by using photolithographic techniques, such as techniques where a micro mirror device is used to expose visible light to spatial selected features on a microarray as explained above.

It has been shown that the deprotection reaction is dependent on the solvent used during the peptide synthesis process. Solvents known by the skilled person can be used during peptide synthesis. For example, polar solvents like dimethylsulfoxide (DMSO), n-methylpyrrolidone (NMP), acetonitrile (MeCN) or isopropanol can be used. Said solvents can contain certain additives, such as imidazole, hydroxylamine and water. Imidazole can be added at concentrations of 0.1% to 3% (v/v), 0.5% to 1.5% (v/v), or imidazole can be added at a concentration of 1% (v/v). Hydroxylamine can be added at concentrations of 0.1% to 3% (v/v), 0.2% to 1% (v/v), or hydroxylamine can be added at a concentration of 1% (v/v). Water can be added at concentrations of 0.1% to 20% (v/v), 1% to 17% (v/v), or water can be added at a concentration of 1% (v/v). Examples of useful solvents are DMSO, DMSO+1% imidazole, NMP+ 0.5% hydroxylamine, MeCN+1% H2O, MeCN+1% H2O+ 1% imidazole, isopropanol+1% imidazole, isopropanol+ 12% H2O+1% imidazole.

The PLPG associated with amino acids for peptide synthesis can be used in a concentration within the solvents of 0.1 mmol/L to 0.5 mmol/L, 0.2 mmol/L to 0.4 mmol/L, or the PLPG can be used at a concentration of 0.3 mmol/L.

The PLPG associated with amino acids can be used in connection with sensitizing agents known by the skilled person, which increase the effectiveness of the deprotection reaction.

Oligopeptide microarrays can be used for a variety of purposes, including but not limited to screening of antibody libraries, quantitative or qualitative analysis of biological samples, biomarker discovery, enrichment of scarce proteins, depletion of high abundant proteins, analysis of protein-protein-interactions, analysis of DNA-protein-interactions or RNA-protein-interactions.

In another embodiment compounds according to formula Ib are used for the maskless photolithography based peptide array synthesis as NH-protecting group in amino acids as urethan. The PLPG is used as NH-blocked free acid, activated ester, acid halogenide, anhydride, intermolecular or intramolecular as N-carboxy-anhydride (NCA).

In another embodiment the compounds according to formula Ib are used for the maskless photolithography based peptide array synthesis as COOH-protecting group in amino acids as ester for inverse direction of synthesis.

The PLPG according to the disclosure can further be used in any process known by the skilled person where protected sugars are necessary. The sugars used can be compounds, such as aldohexoses and aldopentoses. In an embodiment, the PLPG as described herein can be used for the synthesis of carbohydrates, glycoproteins and proteoglycans in solution. In some embodiments, the PLPG as described herein can be used for the synthesis of carbohydrates, glycoproteins and proteoglycans on a solid support. The synthesis can be performed by any standard method known in the state of the art. For example, the synthesis can be performed by using photolithographic techniques, such as techniques where a micro mirror device is used to expose visible light to spatial selected features on a microarray as explained above.

Carbohydrate microarrays can be used for a variety of purposes, including but not limited to analysis of saccharide-protein-interactions, high-throughput analysis of proteins and cells, analysis of glycans and their molecular interactions, In another embodiment the compounds according to formula Ib are used for the maskless photolithography based synthesis of carbohydrates, glycoproteins, proteoglycans, and the like, as OH-protecting group as ether.

In another embodiment the compounds according to formula Ib are used as SH-protecting group for orthogonal strategies as ether, ester or thiocarbonate.

In another embodiment the compounds according to formula Ib are used as photoactivable protecting groups for releasing an biologically active structure for the initiation of a polymerase reaction or a ATP-dependent biochemical conversion.

The present disclosure further relates to the use of the compound according to formula Ib, characterized in that light is used for the maskless photolithography having a wavelength of 375 to 405 nm, for example 390 nm.

The present disclosure further relates to a method for producing the diarylsulfide backbone containing PLPG which can be used for the photolithography based oligonucleotide and peptide synthesis, wherein the method comprises the following steps:

a) Providing as a starting material p-Diethylbenzene.

b) Bromination of the phenyl ring in one position by the action of molecular bromine and purification by distillation.

c) Nitration of the obtained compound in Nitric- and Sulfuric Acid in the position para- to the Bromine and isolation and purification by column chromatography on silica gel and crystallization.

d) Hydroxymethylation of the compound by the action of para-Formaldehyde in DMSO and Triton B at the benzylic position.

e) Conversion of the aromatic bromine group to the aryl sulfide by action of the appropriate thiophenol, thionaphthol etc in DMF potassium carbonate and catalytic amounts of copper(II) salt and purification by column chromatography on silica gel.

f) Conversion of the previous alcohol to the chlorocarbonate by action of triphosgen in THF and triethylamine.

g) Reaction of the chlorocarbonate with the appropriate nucleoside and further reacting the nucleoside with a phosphitylating agent to the appropriate phospshoramidite, or reaction of the chlorocarbonate with the appropriate amino acid derivative.

The following examples, including sequences and figures, are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It is understood that modifications can be made in the procedures set forth without departing from the spirit of the disclosure.

EXAMPLES

Example 1

Evaluation of the Half-Life of 5PyS4EtNPPOC-Thymidine in Dependence of the Solvent at a Wavelengths of 390 nm and 404 nm To evaluate the half-life of the PLPG, 5PyS4EtNPPOC-Thymidine was dissolved in a concentration of c=0.3 mmol/L in the solvents given in FIGS. 1 and 2. As solvents dimethylsulfoxide (DMSO), n-methylpyrrolidone (NMP), acetonitrile (MeCN) and isopropanol were used. Imidazole, hydroxylamine or water were added to the solvents as depicted in the table. In case of an irradiation wavelength of 390 nm (FIG. 1), light exposure was performed for 2, 4, 6 s or 2, 4, 6, 8 s or 2, 4, 6, 8, 12 s, respectively, to induce deprotection of threonine. In case of an irradiation wavelength of 404 nm (FIG. 2), light exposure was performed for 1, 2, 3, 4 min or 1, 2, 3, 5 min, respectively, to induce deprotection of thymidine. Subsequently, the solution was analyzed by HPLC in order to evaluate the time period necessary to deprotect 50% of the initial amount of the protected thymidine. The half-lives were then extrapolated from the durations resulting from the exposure times. As can be taken from FIGS. 1 and 2, in case of a wavelengths of 390 nm, fastest deprotection was achieved with DMSO (2.1 s), NMP+0.5% hydroxylamine (1.8 s), MeCN+1% H2O (2.0 s) and isopropanol+12% H2O+1% imidazole (2.2 s). In case of a wavelengths of 404 nm, fastest deprotection was achieved with DMSO+1% imidazole (2.5 min), NMP+0.5% hydroxylamine (1.8 min), MeCN+1% H2O+1% imidazole (2.6 min) and isopropanol+12% H2O+1% imidazole (3.8 min). Concerning the significant time differences between 390 nm (seconds) and 404 nm (minutes), it has to be taken into consideration that in case of the former the power output of the lamp was 15 W, whereas the in case of the latter the power output of the lamp was 0.08 W.

Example 2

UV Absorption Characteristics of PLPG

UV absorption for different PLPG at the wavelengths commonly used is depicted in FIG. 3. The appropriate derivatives of phenylalanine with the PLPG according to the disclosure were dissolved at a concentration of 1 mg/mL in UV grade methanol. UV spectra were recorded in a scanning photometer and absorption values were taken at the given wavelengths. Molar extinction coefficients were calculated from the molecular weight using Lambert Beers law. Deprotection speed of any PLPG is approximately the product of triplett quantum yield times molar extinction coefficient. It may thus be estimated, that PhS-phenylalanine deprotects 15 times more efficient as BTA-phenylalanine and about 25 times more efficient as NPPOC-phenylalanine at an irradiation wavelength 390 nm.

Example 3

Synthesis of a Peptide Array Containing the Target Sequence of an Anti-V5 Antibody Using Disulfide-PLPG-Amino Acids Target-epitope:
(H)GKPIPNPLLGLDST-(OH)

Figure 8:
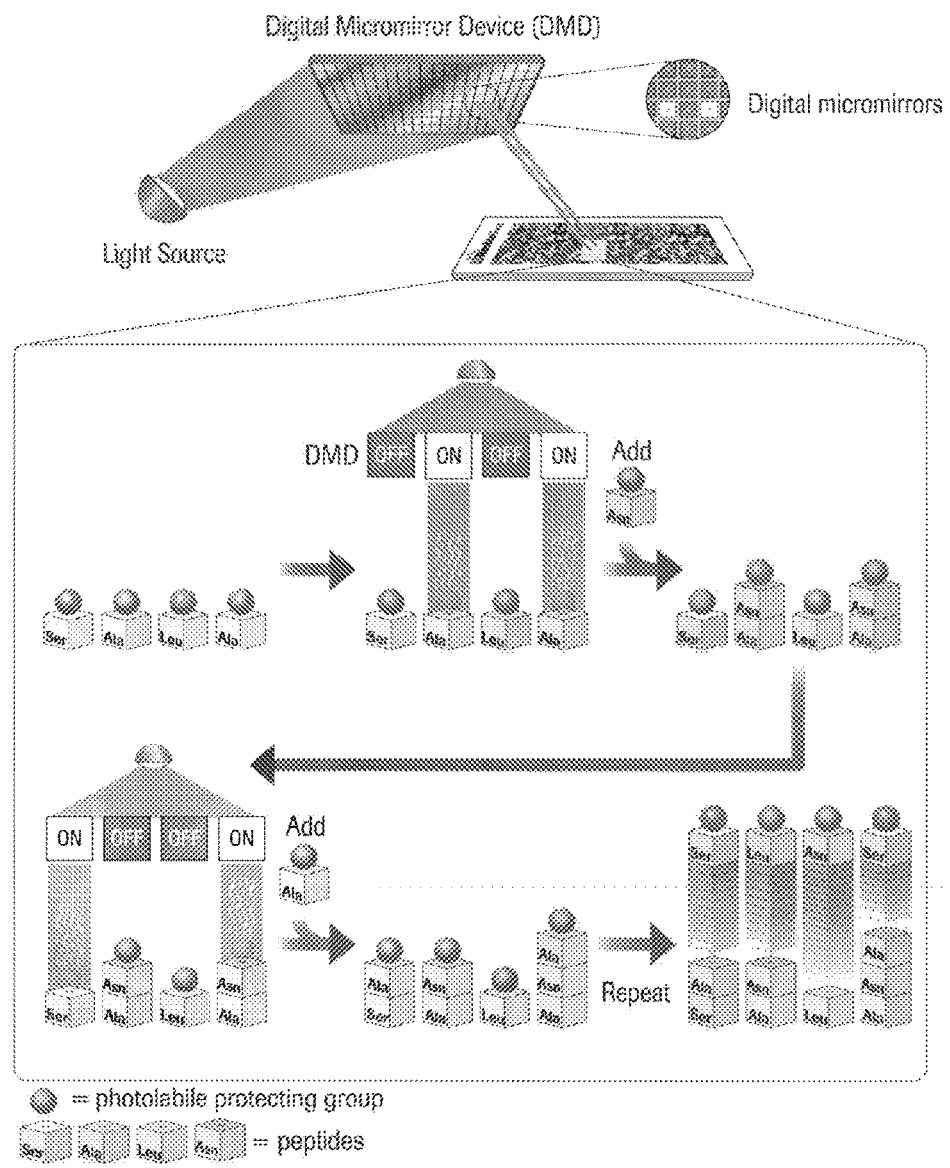
FIG. 8 shows a microarray scan of a peptide array containing the target sequence of an anti-V5 antibody synthesized according to the disclosure using disulfide-PLPG-amino acids.
Figure 8:
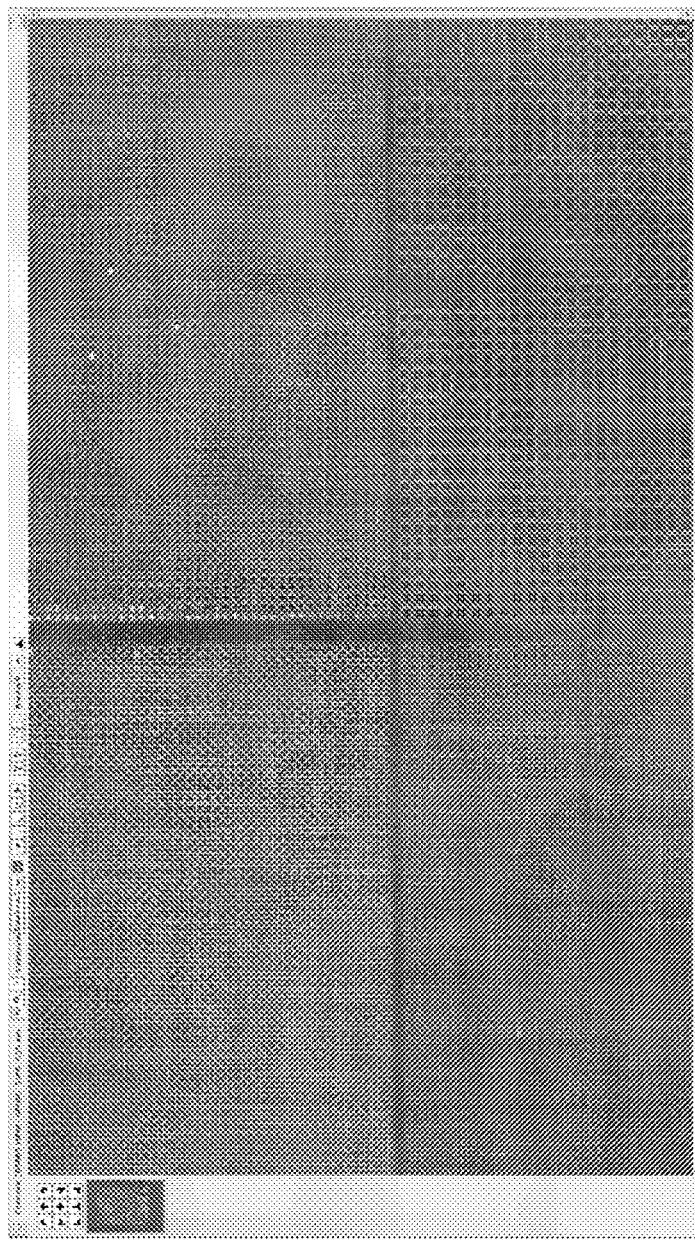
Figure 8:
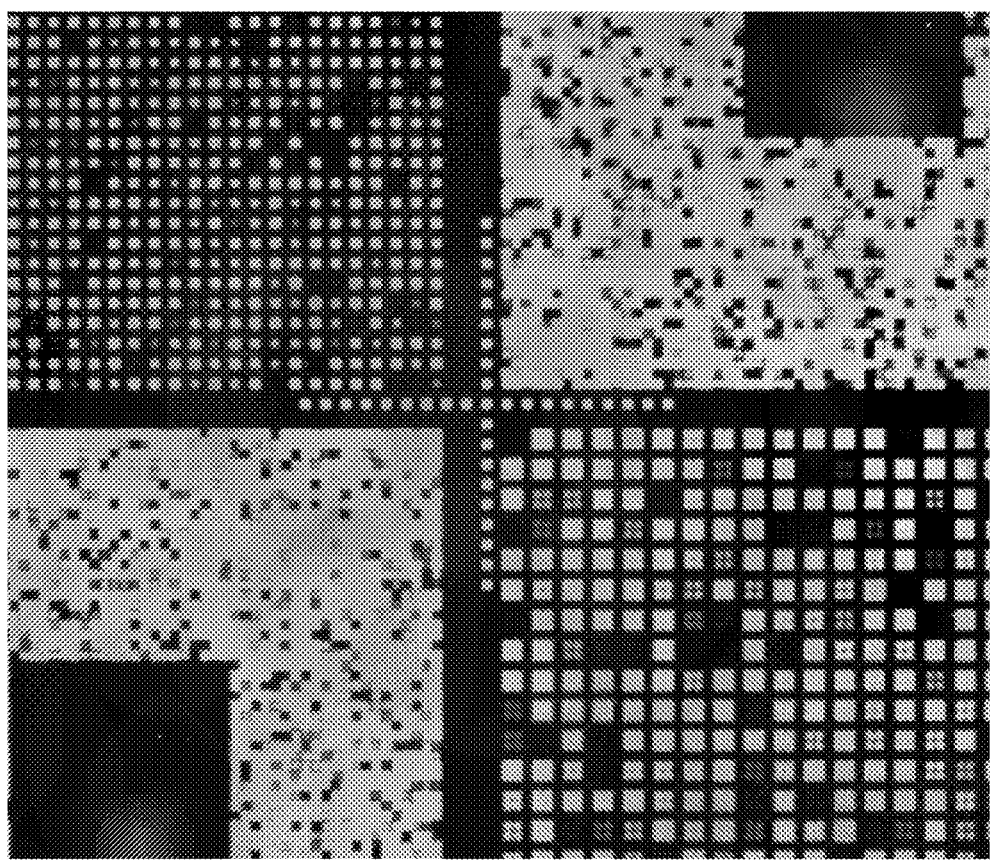

Peptide features on the array were synthesized in a pattern of varying density on a Roche Nimblegen Maskless Array Synthesizer according to the synthesis scheme in FIG. 8, at a light dose of:

Area 1: 2.5 s irradiation at 190 mW/sq·cm [365 nm]
Area 2: 3.5 s irradiation at 190 mW/sq·cm [365 nm]
Area 3: 4.5 s irradiation at 190 mW/sq·cm [365 nm]

Exposure was in NMP/hydroxylamine (1%). The standard irradiation time for NPPOC amino acids at this lamp intensity would have been 50 s. All features of the array contained the same V-5 antigen sequence. Coupling was under standard conditions, 30 mM amino acid, 30 mM activator (HBTU and HOBT) and 60 mM Hünig base in peptide grade DMF sequentially coupled a Greiner 3D-Amino-functionalized microscope slide. Washing between cycles and between coupling and irradiation was with NMP. Final deprotection of the array was achieved by soaking in trifluoro acetic acid, water, triisopropylsilane 97.5:2:0.5 for 1 h. After thorough washing with water, the array was incubated with anti-V5-antibody (labeled with Cy-3 fluorescent dye), obtained from Sigma in the manufacturers recommended buffer system at 1:10 000 dilution (0.1 µg/mL) overnight at room temperature. After washing with buffer and drying the array was scanned at the appropriate filter setting in a Roche Nimblegen MS 200 fluorescent scanner at 2 µm resolution. Images were analyzed in Nimblescan and Genepix (Molecular Dynamics) software packages.

The results show excellent signal intensity over the three doses as shown in FIG. 8b, indicating complete photodeprotection at less than 500 mW*s, whereas NPPOC-amino acids would require about 10.000 mW*s to achieve the same result.

In addition, the same experiment was conducted on a Roche Nimblegen Maskless Array Synthesizer according to the synthesis scheme in FIG. 8a, at a Light Dose of:

Area 1-30: 1-30 s irradiation at 90 mW/sq·cm [390 nm]

Incubation, staining and washing was done as mentioned above.

The results show excellent signal intensity with a maximum at about 21 s irradiation at 390 nm as shown in FIG. 8c, indicating complete photodeprotection at less than 2.000 mW*s, whereas NPPOC-amino acids are insufficiently deprotected at 390 nm and do not give signals attributable to the peptides made.

Example 4

Synthesis of Disulfide-PLPG-Amino Acids

Synthesis pathways are depicted in the respective figures as indicated below.

General Formula of Phenyl-Thio-NPPOC-Amino Acids

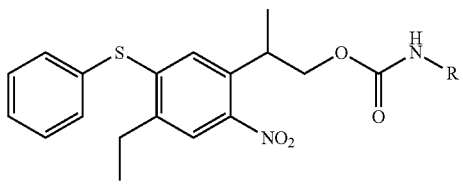

a) 2-(2-Nitro-4-ethyl-5-thiophenyl-phenyl)propanol ("PhSNPPOH")

| 1,4-Diethylbezene | 1902.6 g | 14.18 mol | 1 Eq |
| --- | --- | --- | --- |
| Bromine | 2288 g | 14.32 mol | 1.01 Eq |
| Iron (powder) | 26 g | | |

The corresponding synthesis pathway is depicted in FIG. 4a. A few drops of bromine are added to a mixture of 1902.6 g 1,4-diethylbenzene and 26 g of iron powder. The mixture is stirred at ambient temperature until HBr evolution starts. Then the mixture is cooled in an ice bath and further 2288 g of bromine are added under vigorous stirring over a period of approximately 5 h. Then the ice bath is removed and the mixture is stirred over night at ambient temperature. The reaction mixture is washed with water, saturated $NaHCO_3$ solution and again with water. The crude product is diluted with toluene, concentrated and distilled in vacuum (approximately 5 mbar/82-84° C.).

2740 g 2,5-diethyl-bromobenzene, a colorless liquid, are obtained (yield: 90% of theory).

$^1$H-NMR (300 MHz, DMSO):
7.37 ppm (d, 1H, Ar—H); 7.20 ppm (d, 1H, Ar—H); 7.12 ppm (dd, 1H, Ar—H); 2.65 ppm (q, 2H, Ar—C$\underline{H}_2$—CH$_3$); 2.56 ppm (q, 2H, Ar—C$\underline{H}_2$—CH$_3$), 1.20-1.15 ppm (m, 6H, 2×CH$_3$).

b) 2,5-Diethyl-4-nitro-bromobenzene

| 2,5-Diethyl-bromobenzene | 426 g | 2 mol |
| --- | --- | --- |
| HNO$_3$ (65%) | 202 ml | |
| H$_2$SO$_4$ conc. | 241 ml | |

The corresponding synthesis pathway is depicted in FIG. 4b. Under ice cooling 241 mL of H2SO4 conc. are added slowly to 202 mL of HNO3 (65%). Under ice cooling and vigorous stirring this mixture is dropped slowly into 426 g of 2,5-diethyl-bromobenzene (dosing time 2 h). The reaction mixture is stirred over night at ambient temperature. Then the mixture is poured on ice, diluted with dichloromethane, washed twice with water and finally with saturated NaHCO$_3$-solution. The organic phase is diluted with toluene, concentrated in vacuum and purified by fast filtration (silica gel, mobile phase iso-hexane).

217 g of a slightly yellow oil are obtained (yield: 42% of theory).

$^1$H-NMR (300 MHz, DMSO):
7.74 ppm (s, 2H, Ar—H); 4.72 ppm (t, 1H, OH); 3.54-3.48 ppm (m, 2H, HO—C$\underline{H}_2$), 3.26-3.14 ppm (m, 1H, HO—CH$_2$—C$\underline{H}$); 2.74 ppm (q, 2H, Ar—C$\underline{H}_2$—CH$_3$); 1.25-1.15 ppm (m, 6H, 2×CH$_3$).

c) 2-(2-Nitro-4-ethyl-5-bromophenyl)propan-1-ol ("BrEtNPPOH")

| 2,5-Diethyl-4-nitro-bromobenzene | 1000 g | 3.87 mol | 1 Eq |
| --- | --- | --- | --- |
| Paraformaldehyde | 418.8 g | 4.65 mol | 1.2 Eq |
| Triton B (40% in methanol) | 1090 ml | | |
| DMSO | 5.2 l | | |
| Acetic Acid | 400 ml | | |

The corresponding synthesis pathway is depicted in FIG. 4c. A mixture of 1000 g 2,5-diethyl-4-nitro-bromobenzene, 418.8 g paraformaldehyde, 1090 mL triton B (40% in methanol) and 5.2 L DMSO is heated for 2 h at 80 to 90° C. The heating is switched off and the mixture is stirred for further 4 h. 400 mL of acetic acid are added. The mixture is diluted with water to a volume of approximately 15 L and extracted twice with 2 L of toluene. The toluene extract is washed twice with 1 L of water and then concentrated in vacuum. The crude product is purified by chromatography (silica gel, gradient: iso-hexane to iso-hexane/EtOAc 30%).

Yield: 521 g 2-(2-Nitro-4-ethyl-5-bromophenyl)propan-1-ol as a brown oil (46% of theory) plus 77 g of lesser purity.

$^1$H-NMR (300 MHz, DMSO):
7.74 ppm (s, 2H, Ar—H); 4.72 ppm (t, 1H, OH); 3.54-3.48 ppm (m, 2H, HO—C$\underline{H}_2$), 3.26-3.14 ppm (m, 1H, HO—CH$_2$—C$\underline{H}$); 2.74 ppm (q, 2H, Ar—C$\underline{H}_2$—CH$_3$); 1.25-1.15 ppm (m, 6H, 2×CH$_3$).

d) 2-(2-Nitro-4-ethyl-5-thiophenylphenyl)propanol (PhSNPPOH)

| BrEtNPPOH | 450 g | 1.56 mol | 1 Eq |
| --- | --- | --- | --- |
| Thiophenol | 172 g | 156 mol | 1 Eq |
| K$_2$CO$_3$ | 324 g | 2.34 mol | 1.5 Eq |
| DMF | 2 L | | |

The corresponding synthesis pathway is depicted in FIG. 4d. A mixture oft the reactants and DMF was stirred at 140-160° C. for 5 h. After cooling to 110° C., the solvent is removed by distillation under vacuum. The residue was treated with approximately 2.5 L water and extracted with approximately 1 L dichlormethane. The organic phase was washed with dilute NaOH and water, then evaporated to dryness in vacuo, further distilled with an azeotropic toluene/ethanol-mixture and purified by column chromatography on silica gel in 5 to 30% ethylacetate in hexanes.

Yield: 352 g clear, yellow oil (71%)

e) 2-(2-Nitro-4-ethyl-5-thiophenylphenyl)propanol chlorocarbonate ("PhSNPPOC-Cl")

| PhSNPPOH | 352 g | 1.11 mol | 1 Eq |
| --- | --- | --- | --- |
| Triethylamin | 112.2 g | 1.11 mol | 1 Eq |

| Triphosgen | 219.4 g | 2.22 mol Phosgen | 2 Eq |
| THF | ca. 1.7 L | | |

The corresponding synthesis pathway is depicted in FIG. 4e. 219.4 g triphosgene was dissolved in 1 L dry THF under stirring for 30 min. Under ice-cooling, a solution of 352 g PhSNPPOH and 112.2 g NEt3 in 700 mL dry THF was added slowly over a period of 3 h. After standing overnight, the icebath was replaced by a water bath at 40° C. and excess phosgen and about 1 L THF removed in vacuo. The suspension was filtered, the residue washed with little THF and filtrates evaporated to dryness in vacuo.

Yield: 410.3 g yellow crystals (97%)

The material is pure for further use without purification.

f) PhSNPPOC-Glvycine-OH

| Glycine | 5.81 g | 0.0774 mol | 1 Eq |
| PhSNPPOC-Cl | 29.4 g | 0.0774 mol | 1 Eq |
| Na₂CO₃ | 18.1 g | 0.1703 mol | 2.2 Eq |
| Water | 190 mL | | |
| THF | 150 mL | | |

The corresponding synthesis pathway is depicted in FIG. 4f. 5.81 g glycine und 18.1 g Na2CO3 are dissolved in 190 mL water and 60 mL THF. The solution is stirred in an ice-bath and is dropwise treated with a solution of 29.4 g PhSNPPOC-Cl in 90 mL THF. Stirring is continued for 20 min. THF was evaporated and the solution adjusted to pH 11. The solution is extracted twice with approximately 500 mL Hexane/Ethylacetate 1:1, the pH is adjusted to 2.5 with dilute HCl and extracted with approximately 500 mL ethylacetate. The organic phase is washed with approximately 500 mL water and evaporated to dryness. The product is purified by column chromatography on silica gel with methanol in dichlormethane (0 to 3%).

Yield: 21 g pale yellow amorphous foam (65%)

g) PhSNPPOC-Proline-OH

| Proline | 8.6 g | 0.075 mol | 1 Eq |
| PhSNPPOC-Cl | 28.5 g | 0.075 mol | 1 Eq |
| Na₂CO₃ | 17.5 g | 0.165 mol | 2.2 Eq |
| Water | 1000 ml | | |
| THF | 1200 ml | | |

The corresponding synthesis pathway is depicted in FIG. 4g. 8.6 g proline and 17.5 g Na2CO3 are dissolved in 1000 mL water and 1000 mL THF. The solution is stirred in an ice-bath and is dropwise treated with a solution of 28.5 g PhSNPPOC-Cl in 200 mL THF. Stirring is continued for 20 min. THF was evaporated and the solution adjusted to pH 11. The solution is extracted twice with approximately 500 mL ethylacetate, the pH is adjusted to 2.5 with dilute HCl and extracted with approximately 500 mL ethylacetate. The organic phase is washed with approximately 500 mL water and evaporated to dryness. The product is purified by column chromatography on silica gel with methanol in dichlormethane (0 to 2%).

Yield: 21.7 g pale yellow amorphous foam (63%)

h) PhSNPPOC-Isoleucine-OH

| Isoleucine | 9.97 g | 0.076 mol | 1 Eq |
| PhSNPPOC-Cl | 28.9 g | 0.076 mol | 1 Eq |
| Na₂CO₃ | 26.8 g | 0.25 mol | 3.3 Eq |
| Water | 300 ml | | |
| THF | 300 ml | | |

The corresponding synthesis pathway is depicted in FIG. 4h. 9.97 g isoleucin and 26.8 g Na2CO3 are dissolved in 300 mL water and 200 mL THF. The solution is stirred in an ice-bath and is dropwise treated with a solution of 28.9 g PhSNPPOC-Cl in 90 mL THF. Stirring is continued for 20 min. THF was evaporated and the pH of the solution adjusted to 9.5.

The solution is extracted twice with approximately 500 mL hexane/ethylacetate 1:1, the pH is adjusted to 3.2 with dilute HCl and extracted with approximately 500 mL ethylacetate. The organic phase is washed with approximately 500 mL water and evaporated to dryness. The product is purified by column chromatography on silica gel with methanol in dichlormethane (0 to 2%).

Yield: 15 g pale yellow oil (42%)

i) PhSNPPOC-AsparticAcid-OH

| Aspartate | 10.5 g | 0.0789 mol | 1 Eq |
| PhSNPPOC—Cl | 30.0 g | 0.0789 mol | 1 Eq |
| Na₂CO₃ | 23.0 g | 0.22 mol | 2.8 Eq |
| Water | 1000 ml | | |
| THF | 1200 ml | | |

The corresponding synthesis pathway is depicted in FIG. 4i. 10.5 g aspartate and 23 g Na2CO3 are dissolved in 1000 mL water and 1000 mL THF. The solution is stirred in an ice-bath and is dropwise treated with a solution of 30 g PhSNPPOC-Cl in 200 mL THF. Stirring is continued for 20 min. THF was evaporated. The solution is extracted twice with approximately 500 mL hexane/ethylacetate 1:1, the pH is adjusted to 2 with dilute HCl and extracted with approximately 500 mL ethylacetate. The organic phase is washed with approximately 500 mL Water and evaporated to dryness. The product is purified by column chromatography on silica gel with methanol in dichlormethane (0 to 2%).

Yield: 28 g pale yellow amorphous foam (74%)

j) PhSNPPOC-Asparagine-OH

| Asparagine | 12.7 g | 0.0848 mol | 1 Eq |
| PhSNPPOC—Cl | 32.2 g | 0.0848 mol | 1 Eq |
| Na₂CO₃ | 19.8 g | 0.1866 mol | 2.2 Eq |
| Wasser | 1000 ml | | |
| THF | 1200 ml | | |

The corresponding synthesis pathway is depicted in FIG. 4j. 12.7 g asparagine and 19.8 g Na2CO3 are dissolved in 1000 mL water and 1000 mL THF. The solution is stirred in an ice-bath and is dropwise treated with a solution of 32.2 g PhSNPPOC-Cl in 200 mL THF. Stirring is continued for 20 min. THF was evaporated. The solution is extracted twice with approximately 500 mL ether, the pH is adjusted to 2 with dilute HCl and extracted with approximately 500 mL ethylacetate. The organic phase is washed with approximately 500 mL water and evaporated to dryness. The product is purified by crystallization from ethylacetate.

Yield: 28 g pale yellow crystals (73%)

k) PhSNPPOC-Leucine-OH

| Leucine | 12.1 g | 0.092 mol | 1 Eq |
| --- | --- | --- | --- |
| PhSNPPOC—Cl | 35.0 g | 0.092 mol | 1 Eq |
| Na₂CO₃ | 21.5 g | 0.202 mol | 2.2 Eq |
| Water | 250 ml | | |
| THF | 250 ml | | |

The corresponding synthesis pathway is depicted in FIG. 4k. 12.1 g leucine and 21.5 g Na2CO3 are dissolved in 250 mL water and 200 mL THF. The solution is stirred in an ice-bath and is dropwise treated with a solution of 35 g PhSNPPOC-Cl in 50 mL THF. Stirring is continued for 20 min. THF was evaporated. The solution is extracted twice with approximately 300 mL hexane/ethylacetate 1:1, the pH is adjusted to 3 with dilute HCl and extracted with approximately 500 mL ethylacetate. The organic phase is washed with approximately 500 mL water and evaporated to dryness. The product is purified by column chromatography on silica gel with methanol in dichlormethane (0 to 3%).

Yield: 40 g yellow oil (91%)

l) PhSNPPOC-C₆-Spacer

| 6-Amino-hexanoic Acid | 3.45 g | 0.0263 mol | 1 Eq |
| --- | --- | --- | --- |
| PhSNPPOC—Cl | 10.0 g | 0.0263 mol | 1 Eq |
| Na₂CO₃ | 6.1 g | 0.0579 mol | 2.2 Eq |
| Water | 300 ml | | |
| THF | 200 ml | | |

The corresponding synthesis pathway is depicted in FIG. 4l. 3.45 g 6-Amino-hexanoic Acid and 6.1 g Na2CO3 are dissolved in 300 mL water and 120 mL THF. The solution is stirred in an ice-bath and is dropwise treated with a solution of 10 g PhSNPPOC-Cl in 80 mL THF. Stirring is continued for 20 min. THF was evaporated. The pH was adjusted to 10.5. The solution is extracted twice with approximately 300 mL ether, the pH is adjusted to 2.3 with dilute HCl and extracted with approximately 500 mL ethylacetate. The organic phase is washed with approximately 500 mL water and evaporated to dryness. The product is purified by column chromatography on silica gel with methanol in dichlormethane (0 to 5% and acetic acid 0.5%).

Yield: 10.4 g pale yellow oil (83%)

m) PhSNPPOC-Lysine(Boc)-OH

| Fmoc-Lysine(Boc)-OH | 37.0 g | 0.079 mol | 1 Eq |
| --- | --- | --- | --- |
| Piperidine | 33.6 g | 0.395 mol | 5 Eq |
| THF | 1400 ml | | |
| Na₂CO₃ | 18.4 g | 0.174 mol | 2.2 Eq |
| PhSNPPOC—Cl | 30.0 g | 0.079 mol | 1 Eq |

37.0 g Fmoc-lysine(Boc)-OH are dissolved in 400 ml THF and treated with 33.6 g piperidine for 3 h under stirring with a mechanical stirrer blade. TLC indicated complete FMOC removal after that period. Water (approximately 2 L) was added and stirred for another 30 min. The precipitate was filtered with suction. The clear filtrate was charged with 18.4 g Na2CO3 and evaporated to dryness. Evaporation was continued until all piperidine was removed, by repeatedly addition of water and distillation. The residue was dissolved in approximately 1 L water and treated with 800 mL THF. The solution is stirred in an ice-bath and is dropwise treated with a solution of 30 g PhSNPPOC-Cl in 200 mL THF. Stirring is continued for 20 min. THF was evaporated. The pH is adjusted to 2 with dilute HCl and extracted with approximately 500 mL ethylacetate. The organic phase is washed with approximately 500 mL Water and evaporated to dryness. The product is purified by column chromatography on silica gel with methanol in dichlormethane (0 to 1%).

Yield: 28.3 g pale orange amorphous foam (60%)

n) PhSNPPOC-Serine(t-Bu)-OH

| Fmoc-Serine(t-Bu)-OH | 30.3 g | 0.079 mol | 1 Eq |
| --- | --- | --- | --- |
| Piperidine | 33.6 g | 0.395 mol | 5 Eq |
| THF | 1600 ml | | |
| Na₂CO₃ | 18.4 g | 0.174 mol | 2.2 Eq |
| PhSNPPOC—Cl | 30.0 g | 0.079 mol | 1 Eq |

30.3 g Fmoc-Serine(Boc)-OH are dissolved in 600 mL THF and treated with 33.6 g piperidine for 3 h under stirring with a mechanical stirrer blade. TLC indicated complete FMOC removal after that period. Water (approximately 2 L) was added and stirred for another 60 min. The precipitate was filtered with suction. The clear filtrate was charged with 18.4 g Na2CO3 and evaporated to dryness. Evaporation was continued until all piperidine was removed, by repeatedly addition of water and distillation. The residue was dissolved in approximately 600 mL water, filtered and treated with 800 mL THF. The solution is stirred in an ice-bath and is dropwise treated with a solution of 30 g PhSNPPOC-Cl in 200 ml THF. Stirring is continued for 20 min. THF was evaporated. The pH is adjusted to 2 with dilute HCl and extracted with approximately 500 mL ethylacetate. The organic phase is washed with approximately 500 mL water and evaporated to dryness. The product is purified by column chromatography on silica gel with 1% methanol in dichlormethane.

Yield: 30.9 g pale yellow amorphous foam (77%)

o) PhSNPPOC-Threonine(t-Bu)-OH

| Fmoc-Thr(t-Bu)-OH | 31.4 g | 0.079 mol | 1 Eq |
| --- | --- | --- | --- |
| Piperidin | 33.6 g | 0.395 mol | 5 Eq |
| THF | 1300 ml | | |
| Na₂CO₃ | 18.4 g | 0.174 mol | 2.2 Eq |
| PhSNPPOC—Cl | 30.0 g | 0.079 mol | 1 Eq |

31.4 g Fmoc-Thr(t-Bu)-OH are dissolved in 600 mL THF and treated with 33.6 g piperidine for 4 h under stirring with a mechanical stirrer blade. TLC indicated complete FMOC removal after that period. Water (approximately 3 L) was added and stirred for another 30 min. The precipitate was filtered with suction. The clear filtrate was charged with 18.4 g Na2CO3 and evaporated to dryness. Evaporation was continued until all piperidine was removed, by repeatedly addition of water and distillation. The residue was dissolved in approximately 600 mL Water, filtered and treated with 600 mL THF. The solution is stirred in an ice-bath and is dropwise treated with a solution of 30 g PhSNPPOC-Cl in 100 mL THF. Stirring is continued for 20 min. THF was evaporated. The pH is adjusted to 2 with dilute HCl and extracted with approximately 500 mL ethylacetate. The organic phase is washed with approximately 500 ml water and evaporated to dryness. The product is purified by column chromatography on silica gel with 1% methanol in dichlormethane.

Yield: 30.9 g pale yellow amorphous foam (69%)

p) PhSNPPOC-Histidine(Trt)-OH

Step 1:

| | | | |
|---|---|---|---|
| Fmoc-His(Trt)-OH | 100 g | 0.161 mol | 1 Eq |
| Piperidine | 140 g | 1.614 mol | 10 Eq |
| THF | 2000 ml | | |

100 g Fmoc-His(Trt)-OH are dissolved in 2000 mL THF and treated with 140 g piperidine for 2 h under stirring with a mechanical stirrer blade. TLC indicated complete FMOC removal after that period.

Water (approximately 4 L) was added and stirred for another 30 minutes. The precipitate was filtered with suction. The clear filtrate was concentrated to remove all THF. The pH was adjusted to 2.5 with dilute HCl and the mixture stirred overnight.

Filtration yielded 53 g colorless crystals (83%), which were dried in the air overnight.

Step 2:

| | | | |
|---|---|---|---|
| H-His(Trt)-OH | 20.9 g | 0.0526 mol | 1 Eq |
| PhSNPPOC—Cl | 20.0 g | 0.0526 mol | 1 Eq |
| $Na_2CO_3$ | 12.3 g | 0.116 mol | 2.2 Eq |
| THF | 800 ml | | |

The crystals from above, 20 g, and 12.3 g Na2CO3 were dissolved in approximately 800 mL water and 700 mL THF. The solution is stirred in an ice-bath and is dropwise treated with a solution of 20 g PhSNPPOC-Cl in 100 mL THF. Stirring is continued for 20 min. THF was evaporated. The pH is adjusted to 1.5 with dilute HCl and extracted with approximately 500 mL ethylacetate. The organic phase is washed with approximately 500 mL water and evaporated to dryness. The product is purified by column chromatography on silica gel with 0-1% methanol in dichlormethane and acetic acid (0.01%).

Yield: 10 g pale amorphous foam (26%)

Example 5

Synthesis of Disulfide-PLPG-Nucleotides

5'-PhSNPPOC-dB-3'-PA's a) 5'-PhSNPPOC-dT

| | | | |
|---|---|---|---|
| Thymidine | 19.1 g | 0.0789 mol | 1 Eq |
| PhSNPPOC—Cl | 30.0 g | 0.0789 mol | 1 Eq |
| Pyridine | 300 ml | | |
| Dichloromethane | 50 ml | | |

A solution of 19.1 g thymidine in 300 mL dry pyridine is stirred in an ice-bath. Dropwise, a solution of 30.0 g PhSNPPOC-Cl in 50 mL dichloromethane is added.

After 10 min continued stirring, the solution is washed twice with 800 mL water and evaporated to dryness. The residue is co-evaporated with a mixture of toluene/ethanol. Purification was accomplished by column chromatography on silica gel in methanol (0 to 2.5%) in dichloromethane.

Yield: 28 g pale yellowish amorphous foam (60%)

b) 5'-PhSNPPOC-dT-3'-PA

| | | | |
|---|---|---|---|
| 5'-PhSNPPOC-dT | 27.1 g | 0.0463 mol | 1 Eq |
| DCI | 2.7 g | 0.0232 mol | 0.5 Eq |
| P-Reagent | 13.5 g | 0.0449 mol | 0.97 Eq |
| Dichloromethane | 300 ml | | |

A mixture of the reactants, vigorously dried and under exclusion of moisture, was stirred overnight at room temperature. Hexane was added until a slight turbidity remains. After 10 min stirring, the precipitate is filtered by suction and the crude product purified by column chromatography on silica gel with a gradient from 65% to 80% ethylacetate in hexane.

Yield: 29.7 g pale yellowish amorphous foam (81%)

P-NMR: 144.4 (m) ppm, 94% pure c) 5'-PhSNPPOC-$dC^{Ac}$

| | | | |
|---|---|---|---|
| $dC^{Ac}$ | 28.3 g | 0.105 mol | 1 Eq |
| PhSNPPOC—Cl | 40 g | 0.105 mol | 1 Eq |
| Pyridin | 650 ml | | |
| Dichlormethan | 100 ml | | |

A solution of 28.3 g N-(acetyl)-2'-deoxy-cytidine was co-evaporated twice with 200 mL pyridine, dissolved in in 250 mL dry pyridine and stirred in an ice-bath. Dropwise, a solution of 40.0 g PhSNPPOC-Cl in 100 mL dichloromethane is added. After 10 min continued stirring, the solution is washed twice with 800 mL water and evaporated to dryness. The residue is co-evaporated with a mixture of toluene/ethanol. Purification was accomplished by column chromatography on silica gel in methanol (0 to 2.5%) in dichloromethane.

Yield: 31 g pale yellowish amorphous foam (48%)

d) 5'-PhSNPPOC-$dC^{Ac}$-3'-PA

| | | | |
|---|---|---|---|
| 5'-PhSNPPOC-$dC^{Ac}$ | 29.0 g | 0.0473 mol | 1 Eq |
| DCI | 2.8 g | 0.0237 mol | 0.5 Eq |
| P-Reagent | 13.8 g | 0.0459 mol | 0.97 Eq |
| Dichloromethane | 300 ml | | |

A mixture of the reactants, vigorously dried and under exclusion of moisture, was stirred overnight at room temperature. Hexane was added until a slight turbidity remains. The crude product is purified by column chromatography on silica gel with a gradient from 65% to 80% ethylacetate in hexane.

Yield: 21.5 g pale yellowish amorphous foam (56%)

P-NMR: 144.6 (m) ppm, 99% pure e) 5'-PhSNPPOC-dA$^{tac}$

| | | | |
|---|---|---|---|
| dA$^{tac}$ | 46.3 g | 0.105 mol | 1 Eq |
| PhSNPPOC—Cl | 40 g | 0.105 mol | 1 Eq |
| Pyridine | 650 ml | | |
| Dichloromethane | 100 ml | | |

A solution of 46.3 g N-(tert-butyl-phenoxyacetyl)-2'-deoxy-adenosine was co-evaporated twice with 200 mL pyridine, dissolved in in 250 mL dry pyridine and stirred in an ice-bath. Dropwise, a solution of 40.0 g PhSNPPOC-Cl in 100 mL dichloromethane is added. After 10 min continued stirring, the solution is washed twice with 800 mL sodium bicarbonate solution and water and evaporated to dryness. The residue is co-evaporated with a mixture of toluene/ethanol. Purification was accomplished by column chromatography on silica gel in methanol (0 to 1.5%) in dichloromethane.

Yield: 35 g pale yellowish amorphous foam (42%)

f) 5'-PhSNPPOC-dA$^{tac}$-3'-PA

| | | | |
|---|---|---|---|
| 5'-PhSNPPOC-dA$^{tac}$ | 32.3 g | 0.0412 mol | 1 Eq |
| DCI | 2.4 g | 0.0206 mol | 0.5 Eq |
| P-Reagent | 12.0 g | 0.0399 mol | 0.97 Eq |
| Dichloromethane | 300 ml | | |

A mixture of the reactants, vigorously dried and under exclusion of moisture, was stirred overnight at room temperature. Hexane was added until a slight turbidity remains. After 10 min stirring, the precipitate is filtered by suction and the crude product purified by column chromatography on silica gel with a gradient from 50% to 65% ethylacetate in hexane.

Yield: 32 g pale yellowish amorphous foam (79%)
P-NMR: 144.3 (m) ppm, 99% pure g) 5'-PhSNPPOC-dG$^{tac}$

| | | | |
|---|---|---|---|
| dG$^{tac}$ | 48.2 g | 0.105 mol | 1 Eq |
| PhSNPPOC—Cl | 40 g | 0.105 mol | 1 Eq |
| Pyridin | 800 ml | | |
| Dichlormethan | 60 ml | | |

A solution of 48.2 g N-(tert-butyl-phenoxyacetyl)-2'-deoxy-guanosine was co-evaporated twice with 200 mL pyridine, dissolved in in 400 mL dry pyridine and stirred in an ice-bath. Dropwise, a solution of 40.0 g PhSNPPOC-Cl in 600 mL dichloromethane is added. After 10 min continued stirring, the solution is washed twice with 800 mL water and evaporated to dryness. The residue is co-evaporated with a mixture of toluene/ethanol. Purification was accomplished by column chromatography on silica gel in methanol (0 to 5%) in dichloromethane.

Yield: 35 g pale yellowish amorphous foam (42%)

h) 5'-PhSNPPOC-dG$^{tac}$-3'-PA

| | | | |
|---|---|---|---|
| 5'-PhSNPPOC-dG$^{tac}$ | 34.0 g | 0.0425 mol | 1 Eq |
| DCI | 2.5 g | 0.0212 mol | 0.5 Eq |
| P-Reagent | 12.4 g | 0.0412 mol | 0.97 Eq |
| Dichloromethane | 500 mL | | |

A mixture of the reactants, vigorously dried and under exclusion of moisture, was stirred overnight at room temperature. Hexane was added until a slight turbidity remains. The crude product is purified by column chromatography on silica gel with a gradient from 50% to 65% ethylacetate in hexane.

Yield: 24.5 g pale yellowish amorphous foam (58%)
P-NMR: 144.5 (m) ppm, 98% pure Example 6

Synthesis of Further Diarylsulfide PLPG According to the Disclosure a) 5-(t-Butylphenyl-thio)-4-ethyl-2-nitrophenyl-2'-propan-1'-ol (t-Butylthio-NPPOH)

| | | | |
|---|---|---|---|
| 4-t-Bu-Thiophenol | 25.0 g | 0.150 mol | 1.1 Eq |
| BrEt-NPPOH | 39.0 g | 0.135 mol | 1 Eq |
| K$_2$CO$_3$ | 31.1 g | 0.225 mol | 1.7 Eq |
| DMF | 200 mL | | |

A mixture of the reactants was stirred at 100° C. for 3 h. DMF was distilled off in vacuo. The residue was dissolved in dichloromethane, washed twice with water and evaporated to dryness in vacuo. The obtained residue was suspended in hexanes, stirred overnight and filtered off by suction. The crystals were dried.

Yield: 43 g pale yellow powder (85%)
$^1$H-NMR (300 MHz, DMSO):
7.72 ppm (s, 1H, Nitro-Ar—H); 7.50 ppm (m, 2H, Ar—H t-Bu-Ph); 7.38 ppm (m, 2H, Ar—H t-Bu-Ph); 6.88 ppm (s, 1H, Nitro-Ar—H); 4.67 ppm (s, 1H, OH); 3.25-3.21 ppm (m, 3H, Ar—CH(Me)-CH$_2$—OH); 2.73 ppm (q, 2H, Ar—CH$_2$—CH$_3$); 1.29 ppm (s, 9H, CH$_3$ t-Bu); 1.20 ppm (t, 3H, Ar—CH$_2$—CH$_3$; 0.95 ppm (d, 3H, Ar—CH(CH$_3$)—CH$_2$—OH)

b) Naphthyl-thio-NPPOH

| | | | |
|---|---|---|---|
| BrEt-NPPOH | 20.6 g | 0.0715 mol | 1 Eq |
| 2-Thionaphtol | 11.5 g | 0.0715 mol | 1 Eq |
| Kaliumcarbonat | 14.8 g | 0.107 mol | 1.5 Eq |
| DMF | 100 mL | | |

A mixture of the reactants was refluxed for 1.5 h and further stirred overnight at room temperature. The residue was diluted with 1.5 L water and extracted with dichloromethane. The organic extract was washed twice with water, evaporated to dryness in vacuo and purified by column chromatography on silica gel with ethylacetate (0-30%) in hexane.

Yield: 9.0 g yellow oil (34%)
$^1$H-NMR (300 MHz, DMSO):
8.07 ppm (m, 1H, Naphthyl-H), 8.00-7.90 ppm (m, 3H, Naphthyl-H); 7.77 ppm (s, 1H, Nitroaromatic-H); 7.61-7.54 ppm (m, 2H, Naphthyl-H); 7.47-7.41 ppm (m, 1H, Naphthyl-H); 7.11 ppm (s, 1H, Nitroaromatic-H); 4.65 ppm (t, 1H, OH); 3.30-3.15 ppm (m, 3H, Ar—C<u>H</u>(CH$_3$)—C<u>H</u>$_2$—OH); 2.77 ppm (q, 2H, Ar—C<u>H</u>$_2$—CH$_3$); 1.21 ppm (t, 3H, Ar—CH$_2$—C<u>H</u>$_3$); 0.92 ppm (d, Ar—CH(C<u>H</u>$_3$)—CH$_2$—OH)

c) Nitrobenzimidazol-S—NPPOH

| | | | |
|---|---|---|---|
| BrEt-NPPOH | 6.0 g | 0.0208 mol | 1 Eq |
| 2-Merkapto-5-nitro-benzimidazol | 4.06 g | 0.0208 mol | 1 Eq |
| Kaliumcarbonat | 4.3 g | 0.0312 mol | 1.5 Eq |
| DMF | 50 mL | | |

A mixture of the reactants was refluxed for 3 h and further stirred overnight at room temperature. The residue was diluted with 0.5 L water and extracted with dichloromethane. The organic extract was washed twice with water, evaporated to dryness in vacuo and purified by column chromatography on silica gel with ethylacetate (0-30%) in hexane.

Yield: 5.8 g yellow oil (69%)
$^1$H-NMR (300 MHz, DMSO):
13.35 ppm (s, 1H, N<u>H</u>); 8.35 ppm (dd, 1H, Nitrobenzimidazole-H); 7.95 ppm (s, 1H, Nitroaromatic-H); 7.75 ppm (s, 1H, Nitroaromatic-H); 7.63 ppm (1H, d, Nitrobenzimidazole-H); 4.71 ppm (s, 1H, O<u>H</u>); 3.47 ppm (d, 2H, HO—C<u>H</u>$_2$); 3.19 ppm (m, 1H, Ar—C<u>H</u>(CH$_3$)—CH$_2$—OH); 2.79 ppm (q, 2H, Ar—C<u>H</u>$_2$—CH$_3$), 1.21-1.15 ppm (m, 6H, 2×C<u>H</u>$_3$)

d) Pyridyl-S—NPPOH

| | | | |
|---|---|---|---|
| BrEt-NPPOH | 133.5 g | 0.463 mol | 1 Eq |
| 2-Merkaptopyridin | 51.5 g | 0.463 mol | 1 Eq |
| Kaliumcarbonat | 96.0 g | 0.695 mol | 1.5 Eq |
| DMF | 600 mL | | |

A mixture of the reactants was stirred at 140° C. for 4 h. DMF was distilled off in vacuo. The residue was dissolved in dichloromethane, washed twice with water and evaporated to an oil in vacuo. The residue was purified by column chromatography on silica gel with ethylacetate (0-30%) in hexane.

Yield: 87.9 g clear yellow oil (60%)
$^1$H-NMR (300 MHz, DMSO):
8.43 ppm (m, 1H, Py-H); 7.82 ppm (s, 1H, Nitroaromatic-); 7.70 ppm (m, 1H, Py-H); 7.65 ppm (s, 1H, Py-H), 7.21 ppm (m, 1H, Py-H); 4.75 ppm (t, 1H, O<u>H</u>); 3.47 ppm (t, 2H, HO—C<u>H</u>$_2$); 3.20 ppm (m, 1H, HO—CH$_2$—C<u>H</u>CH$_3$); 2.72 ppm (q, 1H, C<u>H</u>$_2$—Benzylic); 1.15 (m, 6H, 2×CH$_3$)

e) 2,5-Diethyl-4-phenoxy-nitrobenzene

| | | | |
|---|---|---|---|
| Phenole | 8.0 g | 0.085 mol | 1.1 Eq |
| NaH (60% in Parafine) | 3.4 g | 0.085 mol | 1.1 Eq |
| 4-Bromo-2,5-diethyl-nitrobenze | 20.0 g | 0.078 mol | 1 Eq |
| DMF | 60 ml | | |

Under vigorous stirring 3.4 g of NaH (60% in parafine) was carefully added to a solution of 8.0 g phenole in 60 ml of DMF. When the gas evolution was finished, 20.0 g of 4-bromo-2,5-diethyl-nitrobenzene were added to the mixture. The reaction mixture was stirred for 1.5 h at 170° C.

Then the reaction mixture was cooled to ambient temperature and poured into 600 ml of water. The resulting emulsion was extracted with hexane. The hexane was distilled of and the distillation residue was dried over night in vacuum. The distillation residue was dissolved in hexane and purified by column chromatography (Silica/hexane).

Yield: 2.2 g slightly coloured oil
$^1$H-NMR (DMSO):
7.96 ppm (s, 1H, Ar—H); 7.48-7.40 ppm (m, 2H, Ph-H); 7.25-7.18 ppm (m, 1H, Ph-H); 7.09-7.03 ppm (m, 2H, Ph-H); 6.78 ppm (s, 1H, Ar—H); 2.72 ppm (q, 2H, Ar—C<u>H</u>$_2$—CH$_3$); 2.68 ppm (q, 2H, Ar—C<u>H</u>$_2$—CH$_3$); 1.18 ppm (t, 3H, Ar—CH$_2$—C<u>H</u>$_3$); 1.07 ppm (t, 3H, Ar—CH$_2$—C<u>H</u>$_3$).

Example 7

Alternative Synthesis of the Diarylsulfide-PLPG with R3=H [Formula I]

a) 3-Acetamido-ethylbenzol

| | | |
|---|---|---|
| 3-Ethyl-anilin | 550 g | 4.54 mol |
| Acetanhydride | 1100 mL | |

Within approximately 4 h, 550 g of 3-Ethyl-anilin were added to acetanhydride. The mixture was stirred overnight at room temperature (DC-control hexan/EtOAc 1:1). The reaction mixture was evaporated to dryness in vacuo. The distillation residue was distilled in high vacuum (Temp.: 210° C., Head-Temp.: 145° C.).

Yield: 710 g yellow oil (96%).

b) 3-Acetamido-6-nitro-ethylbenzol

| | | |
|---|---|---|
| 3-Acetamido-ethylbenzol | 237.0 g | 1.452 mol |
| H$_2$SO$_4$ conc. | 622 mL | |
| HNO$_3$ conc. | 91.0 g | |

237.0 g 3-Acetamido-ethylbenzol were added dropwise to 622 mL H2SO4 conc. in that the temperature of the mixture did not exceed 20° C. The mixture was cooled to -30° C. Subsequently, 91.0 g HNO3 conc. were added dropwise, in that the inner temperature of the mixture did not exceed -20° C. The mixture was thawed to -10° C. and poured into 1800 g of ice. The aqueous phase was separated and extracted with 2× 200 mL of ether. The precipitate of 3-acetamido-6-nitro-ethylbenzol was combined to with the ether extracts and dissolved therein. The ether solution was washed with 100 mL of water and evaporated.

c) 3-Ethyl-4-nitro-aniliniumbromide

| | | |
|---|---|---|
| 3-Acetamido-6-nitro-ethylbenzol (raw product) | | approximately 1.45 mol |
| Hydrobromic acid (48%) | | 400 mL |

The raw product was suspended in 400 mL hydrobromic acid (48%) and heated for 0.5 h to boiling (3-ethyl-4-nitro-aniliniumbromide starts to crystallize, which is associated with a significant increase of the reaction volume). The mixture was cooled to room temperature under stirring and subsequently cooled to 5° C. on ice. The suspension was removed by suction, resuspended in 200 mL cold hydrobromic acid (48%) and filtered again, followed by washing on the nutsch filter with approximately 50 mL cold hydrobromic acid (48%).

Yield: 450 g humid product d) 3-Brom-6-nitro-ethylbenzol

| 3-Ethyl-4-nitro-aniliniumbromide (raw product, humid) | ca. 450 g | ca. 1.45 mol |
|---|---|---|
| Hydrobromic acid (48%) | 250 mL | |
| Water | 400 mL | |
| NaNO$_2$ | | 107.6 g |
| Water | 550 mL | |

The humid product of the previous approach was suspended in a solution of 250 mL hydrobromic acid (48%) in 400 mL of water. A solution of 107.6 g NaNO2 was added dropwise to 550 mL water on ice, in that the temperature of the mixture did not exceed 12° C. The mixture was stirred for 30 min at 0° C. and filtered.

Sandmayer-Conversion:

| Diazoniumsalt-solution | ca. 1.45 mol |
|---|---|
| Copper powder | 84.9 g |
| CuSO$_4$ × 5H$_2$O | 212.3 g |
| Hydrobromic acid (48%) | 670 mL |

The diazoniumsalt-solution was added dropwise to a mixture of 84.9 g copper powder, 212.3 g CuSO4×5H2O and 670 mL hydrobromic acid (48%) on ice, in that the temperature of the mixture did not exceed 15° C. The mixture was stirred over night at room temperature, filtered and the organic phase was separated. The aqueous phase was extracted with dichloromethane. The combined organic phases were filtered under usage of a thin layer of silica gel and then evaporated to dryness in vacuo. 167.8 g of raw product was yielded. The distillation residue was distilled in high vacuum (Temp.: 155° C., Head-Temp.: 85° C.).

Yield: 144.3 g yellow oil (43% via 4 steps).

e) 2-(2-Nitro-5-brom-phenyl)propanol

| 3-Bromo-6-nitro-ethylbenzol | 309.6 g | 1.346 mol | 1 Eq |
|---|---|---|---|
| Paraformaldehyd | 42.4 g | 1.413 mol | 1.05 Eq |
| Kalium-tert-Butylat | 37.8 g | 0.337 mol | 0.25 Eq |
| DMSO | 900 mL | | |

To a solution of 309.6 g 3-bromo-6-nitro-ethylbenzol and 42.4 g paraformaldehyde in 300 mL DMSO, 37.8 g potassium-tert-butylat was added in small portions, in that the temperature increased to 40-50° C. The mixture was stirred over night at room temperature. 900 mL toluol was added to the mixture and washed with 3× 450 mL aqueous NaOH (10%) and subsequently with 450 mL water. The organic phase was evaporated to dryness in vacuo. 319 g of raw product was yielded, which was then purified using chromatography:

Column: 700 g silica gel, diameter 8.5 cm, equilibrated with n-hexan. The raw product was dissolved in 100 mL toluol and loaded onto the column. Elution was performed using the following gradient: 2.5 L n-hexan,

| Ethylacetate/n-hexane | 1:100 | 1 L |
|---|---|---|
| | 1:50 | 1.5 L |
| | 1:20 | 1 L |
| | 1:6 | 2 L |
| | 1:5 | 1.5 L |

Yield: 236.06 g 2-(2-Nitro-5-bromo-phenyl)propanol (67%).

f) PhSNPPOH without ethyl-group

| Br—NPPOH | 5.0 g | 0.0192 mol | 1 Eq |
|---|---|---|---|
| Ph—SH | 2.3 g | 0.0211 mol | 1.1 Eq |
| K$_2$CO$_3$ | 4.5 g | 0.0326 mol | 1.7 Eq |
| DMF | 50 mL | | |

A mixture of the above listed components were mixed 3 h at 120° C. and then over night at 70° C. The reaction mixture was evaporated to dryness in vacuo. Dichloromethane was added to the distillation residue and washed with water, with diluted sodium hydroxide and again with water. The organic phase was evaporated and purified using chromatography (Stationary phase: Silica gel equilibrated with iso-hexane; Gradient: iso-hexane/5% ethyl acetate to iso-hexane/20% ethyl acetate).

Yield: 2.7 g red-brown oil (48%).

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method for preparing a diarylsulfide backbone containing one or more photolabile protecting group(s) according to Formula Ib

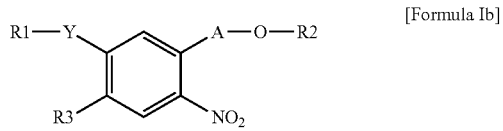

[Formula Ib]

wherein Y is S or O, and

A is selected from the group consisting of —CH$_2$, —CH$_2$—CH$_2$—, —CH(CH$_3$)—, —CH(CH$_3$)—CH$_2$—, and R1 is an unsubstituted or substituted aryl- or heteroaryl-group, and R3 is H, a methyl group or an ethyl group, and wherein R2 is

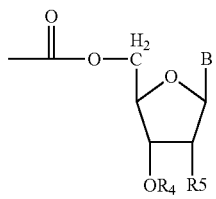
[Formula II]

or wherein R2 is

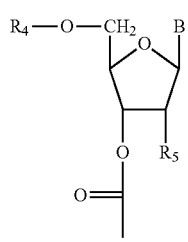
[Formula III]

wherein R4 is H, or R4 with the —O— of Formula III it connects to is a phosphoramidite, H-phosphonate or phosphate triester, and wherein R5 is H, OH, a halogen or XR6, wherein X is O or S and R6 is H, an alkyl-group, aryl-group, or R6 with the —O— of Formula III it connects to is a phosphoramidite, phosphodiester, phosphotriester, H-phosphonate or an acetal or silicone moiety, and wherein B is selected from the group consisting of adenine, cytosine, guanine, thymine, uracil, 2,6-diaminopurine-9-yl, hypoxanthin-9-yl, 5-methylcytosinyl-1-yl, 5-amino-4-imidazolecarboxylic acid-1-yl or 5-amino-4-imidazolecarboxylic acid amide-3-yl, wherein when B is adenine, cytosine or guanine the primary amino group optionally has a protecting group or when B is thymine or uracil at the $O^4$ position is optionally a protecting group, or wherein $R_2$ is

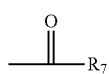
[Formula IV]

wherein R7 is a natural amino acid, a non-natural amino acid or an amino acid derivative, including but not limited to α- or β-amino acids, and formula Ib comprises a urethane bond consisting of a N-terminal nitrogen of R7, the C=O of Formula IV that the N-terminal nitrogen of R7 connects to, and the —O— of formula Ib that the C=O of Formula IV connects to, or wherein R2 with the —O— of formula Ib it connects to is a natural amino acid, a non-natural amino acid or an amino acid derivative, forming an ester bond to formula Ib, including but not limited to α- or β-amino acids, attached to A by an ester bond comprising the —O— of formula Ib and a C-terminal C=O of R2, the method comprising the steps of
a) providing p-diethylbenzene as a starting material;
b) bromination of the phenylring;
c) nitration of the obtained compound in Nitric- and Sulfuric Acid in the position para- to the Bromine;
d) purification and crystallization;
e) hydroxymethylation of the compound at the benzylic position;
f) conversion of the aromatic bromine group to the arylsulfide using thiophenol;
g) purification;
h) conversion of the alcohol to chlorocarbonate; and
i) reaction of the chlorocarbonate with a nucleoside and reaction of the nucleoside with a phosphitylating agent, or
reaction of the chlorocarbonate with an amino acid derivative.

2. The method according to claim 1, characterized in that R1 is a phenyl-group, a tert-butyl-phenyl group, a 1- or 2-naphthyl-group or a 2-pyridyl-group.

3. The method according to claim 1, characterized in that A is —CH(CH$_3$)—CH$_2$—.

4. The method according to claim 1, characterized in that R3 is H or an ethyl group.

5. A method of forming an array through photolithography, said method comprising contacting a substrate having a site activated by exposure to light with a compound of Formula Ib

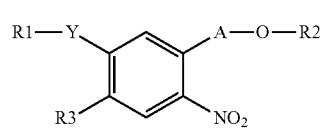
[Formula Ib]

wherein Y is S or O, and
A is selected from the group consisting of —CH$_2$—, —CH$_2$—CH$_2$—, —CH(CH$_3$)—, —CH(CH$_3$)—CH$_2$—, and
R1 is an unsubstituted or substituted aryl- or heteroaryl-group, and R3 is H, a methyl group or an ethyl group, and wherein R2 is

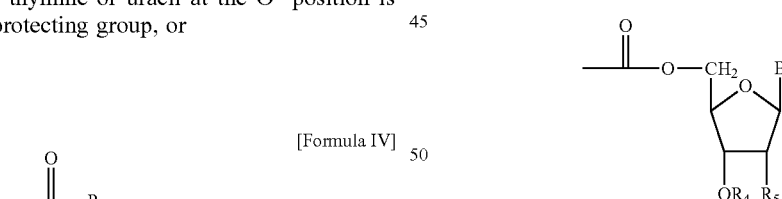
[Formula II]

or wherein R2 is

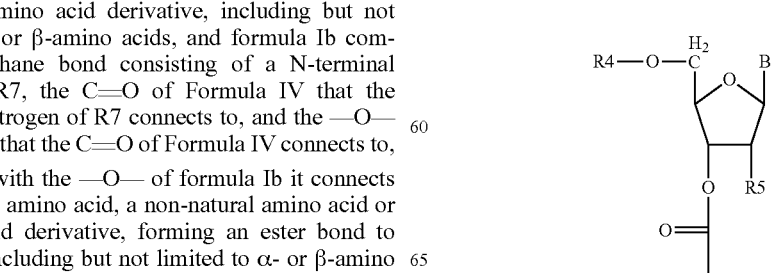
[Formula III]

wherein R4 is H, or R4 with the —O— of Formula III it connects to is a phosphoramidite, H-phosphonate or phosphate triester, and wherein R5 is H, OH, a halogen or XR6, wherein X is O or S and R6 is H, an alkyl-group, aryl-group, or R6 with the —O— of Formula III it connects to is a phosphoramidite, phosphodiester, phosphotriester, H-phosphonate or an acetal or silicone moiety, and wherein B is selected from the group consisting of adenine, cytosine, guanine, thymine, uracil, 2,6-diaminopurine-9-yl, hypoxanthin-9-yl, 5-methylcytosinyl-1-yl, 5-amino-4-imidazolecarboxylic acid-1-yl or 5-amino-4-imidazolecarboxylic acid amide-3-yl, wherein when B is adenine, cytosine or guanine the primary amino group optionally has a protecting group or when B is thymine or uracil at the $0^4$ position is optionally a protecting group, or wherein R2 is

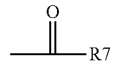

[Formula IV]

wherein R7 is a natural amino acid, a non-natural amino acid or an amino acid derivative, including but not limited to a- or β-amino acids, and formula Ib comprises a urethane bond consisting of a N-terminal nitrogen of R7, the C=O of Formula IV that the N-terminal nitrogen of R7 connects to, and the —O— of formula Ib that the C=O of Formula IV connects to, or wherein R2 with the —O— of formula Ib it connects to is a natural amino acid, a non-natural amino acid or an amino acid derivative, forming an ester bond to formula Ib, including but not limited to α- or β-amino acids, attached to A by an ester bond comprising the —O— of formula Ib and a C-terminal C=O of R2.

6. The method of claim 5 wherein the contacting of the substrate with a compound of Formula Ib produces a DNA microarray or a peptide microarray.

7. The method of claim 6 wherein the method produces a DNA microarray.

8. The method of claim 6 wherein the method produces a peptide microarray.

9. The method of claim 5 wherein the substrate and/or the compound is activated by exposure to light between the wavelengths of 374 to 405 nm.

* * * * *